United States Patent
Taguchi et al.

(10) Patent No.: US 10,813,601 B2
(45) Date of Patent: Oct. 27, 2020

(54) MEDICAL IMAGE PROCESSING APPARATUS, MEDICAL IMAGE PROCESSING METHOD, COMPUTER-READABLE MEDICAL-IMAGE PROCESSING PROGRAM, MOVING-OBJECT TRACKING APPARATUS, AND RADIATION THERAPY SYSTEM

(71) Applicants: KABUSHIKI KAISHA TOSHIBA, Minato-Ku (JP); Toshiba Energy Systems & Solutions Corporation, Kawasaki-Shi (JP)

(72) Inventors: Yasunori Taguchi, Kawasaki (JP); Ryusuke Hirai, Shinagawa (JP); Yukinobu Sakata, Kawasaki (JP); Keiko Okaya, Setagaya (JP); Shinichiro Mori, Sakura (JP)

(73) Assignees: KABUSHIKI KAISHA TOSHIBA, Minato-Ku (JP); Toshiba Energy Systems & Solutions Corporation, Kawasaki-Shi (JP)

( * ) Notice: Subject to any disclaimer, the term of this patent is extended or adjusted under 35 U.S.C. 154(b) by 0 days.

(21) Appl. No.: 16/678,097

(22) Filed: Nov. 8, 2019

(65) Prior Publication Data
US 2020/0069263 A1  Mar. 5, 2020

Related U.S. Application Data
(62) Division of application No. 15/818,057, filed on Nov. 20, 2017, now Pat. No. 10,517,544.

(30) Foreign Application Priority Data
Nov. 21, 2016  (JP) .................................. 2016-226133

(51) Int. Cl.
*G06K 9/00* (2006.01)
*A61B 6/03* (2006.01)
(Continued)

(52) U.S. Cl.
CPC .............. *A61B 6/032* (2013.01); *A61B 6/022* (2013.01); *A61B 6/12* (2013.01); *A61B 6/4014* (2013.01);
(Continued)

(58) Field of Classification Search
CPC ......... A61B 6/032; A61B 8/54; A61B 6/4014; A61B 6/12; A61B 6/022; A61B 8/08;
(Continued)

(56) References Cited

U.S. PATENT DOCUMENTS 5,951,475 A   9/1999  Gueziec
6,307,914 B1  10/2001 Kunieda et al.
(Continued)

FOREIGN PATENT DOCUMENTS

CN   107297030 A    10/2017
JP   2000-167072    6/2000
(Continued)

OTHER PUBLICATIONS

Office Action dated Aug. 20, 2019, in Taiwanese Patent Application No. 108101184 w/English-language Translation.

*Primary Examiner* — Tom Y Lu
(74) *Attorney, Agent, or Firm* — Oblon, McClelland, Maier & Neustadt, L.L.P.

(57) ABSTRACT

A medical image processing apparatus comprising: a first input interface configured to acquire a three-dimensional volume image of an object which is provided with at least one marker, the three-dimensional volume image being generated by imaging the object using a medical examination apparatus; a second input interface configured to
(Continued)

acquire geometry information of an imaging apparatus which is used for imaging the object to generate a fluoroscopic image of the object; and a specific-setting-information generator configured to generate specific setting information based on the three-dimensional volume image and the geometry information, the specific setting information being used for setting of imaging for generating an image depicting the at least one marker or setting of image processing of the image depicting the at least one marker.

10 Claims, 18 Drawing Sheets

(51) Int. Cl.
    *G16H 30/20* (2018.01)
    *A61B 6/00* (2006.01)
    *A61B 6/12* (2006.01)
    *A61B 8/00* (2006.01)
    *G16H 40/63* (2018.01)
    *A61B 6/02* (2006.01)
    *A61B 8/08* (2006.01)
    *G03B 42/02* (2006.01)
    *A61B 5/055* (2006.01)

(52) U.S. Cl.
    CPC .................. *A61B 8/08* (2013.01); *A61B 8/54* (2013.01); *G03B 42/026* (2013.01); *G16H 30/20* (2018.01); *G16H 40/63* (2018.01); *A61B 5/055* (2013.01); *A61B 6/541* (2013.01); *A61B 8/085* (2013.01); *A61B 8/463* (2013.01); *G06T 2207/30096* (2013.01); *G06T 2207/30204* (2013.01)

(58) Field of Classification Search
    CPC ......... A61B 6/541; A61B 8/463; A61B 8/085; A61B 5/055; G03B 42/026; G06T 2207/30204; G06T 2207/30096; G06F 19/321

See application file for complete search history.

(56) References Cited

U.S. PATENT DOCUMENTS

| | | |
|---|---|---|
| 9,265,468 B2 | 2/2016 | Rai |
| 2012/0046928 A1 | 2/2012 | Gibbs et al. |
| 2014/0270365 A1 | 9/2014 | Mostafavi |
| 2015/0327832 A1 | 11/2015 | Hu et al. |
| 2016/0005168 A1 | 1/2016 | Merlet |
| 2016/0148401 A1 | 5/2016 | Hirai et al. |
| 2017/0231591 A1 | 8/2017 | Murata et al. |
| 2018/0008222 A1* | 1/2018 | Chen .................. G06T 7/73 |
| 2018/0035966 A1 | 2/2018 | Merlet |

FOREIGN PATENT DOCUMENTS

| | | |
|---|---|---|
| JP | 2008-507367 A | 3/2008 |
| JP | 2013-078479 A | 5/2013 |
| JP | 2014-236957 A | 12/2014 |
| JP | 2016-131737 A | 7/2016 |
| TW | 201542171 A | 11/2015 |
| TW | 201602709 A | 1/2016 |
| TW | 201625181 A | 7/2016 |

* cited by examiner

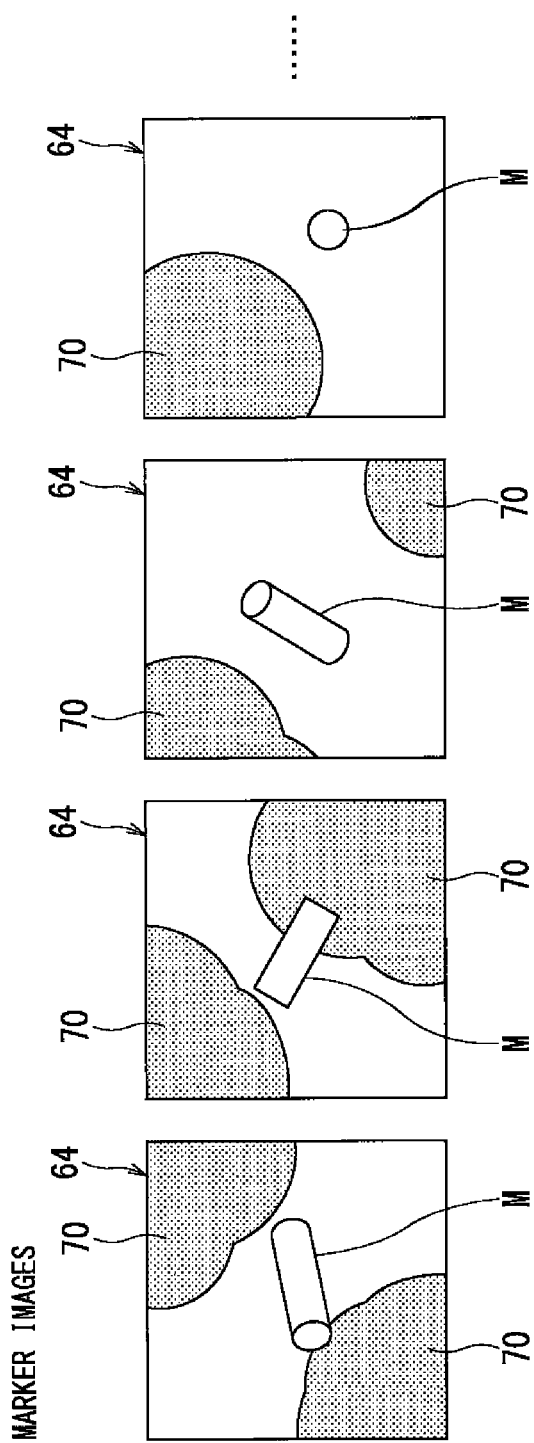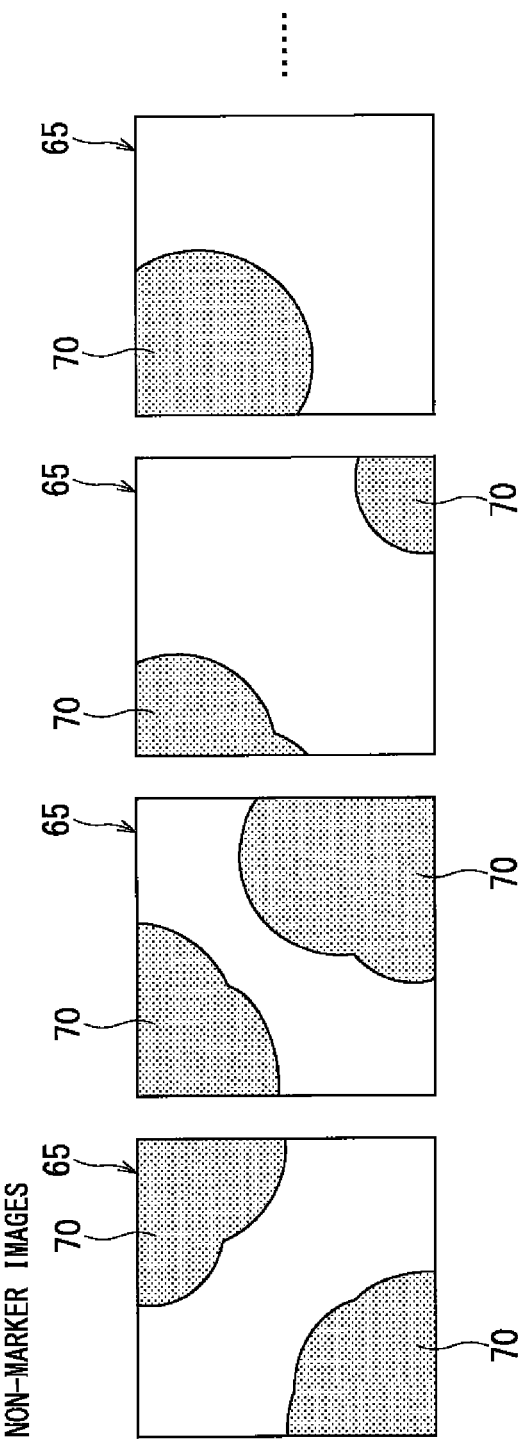

MEDICAL IMAGE PROCESSING APPARATUS, MEDICAL IMAGE PROCESSING METHOD, COMPUTER-READABLE MEDICAL-IMAGE PROCESSING PROGRAM, MOVING-OBJECT TRACKING APPARATUS, AND RADIATION THERAPY SYSTEM

CROSS-REFERENCE TO RELATED APPLICATION

This application is a Divisional of U.S. application Ser. No. 15/818,057 filed Nov. 20, 2017, and claims the benefit of priority of Japanese Patent Application No. 2016-226133, filed on Nov. 21, 2016, the entire contents of each of which are incorporated herein by reference.

FIELD

Embodiments of the present invention relates to medical image processing technology to process a medical image used for a radiation therapy system.

BACKGROUND

Conventionally, when an affected part (i.e., lesion area) of a patient is irradiated with radioactive rays as treatment, the affected part moves in some cases due to movement of the patient such as breathing, heartbeat, and/or intestinal movement. Thus, the affected part is irradiated with radioactive rays under a gated irradiation method using a metal marker or a tracking irradiation method. For instance, by imaging a patient with the use of X-rays during treatment, a fluoroscopic image depicting the marker placed in the vicinity of the affected part is obtained. The movement of the marker is tracked by matching the fluoroscopic image with a template such that the affected part is irradiated at an appropriate timing.

[Patent Document 1] Japanese Unexamined Patent Application Publication No. 2000-167072

In the above-described technique, a user such as a doctor and/or a radiological technician has to set the template while referring to the fluoroscopic image of the patient whose X-ray images are preliminarily generated during treatment planning, which takes time and effort. Further, when the entire range of the fluoroscopic image is processed on a real-time basis in the case of tracking the position of the marker by performing image processing on the fluoroscopic image during treatment, processing load of the CPU increases. Thus, a user has to previously set the range in which the marker is depicted in the fluoroscopic image in order to reduce the load of image processing, and there is a problem that it takes time and effort.

BRIEF DESCRIPTION OF THE DRAWINGS

In the accompanying drawings:

FIG. 17A is a schematic diagram illustrating marker images;

FIG. 17B is a schematic diagram illustrating non-marker images; and

DETAILED DESCRIPTION

Figure 1:
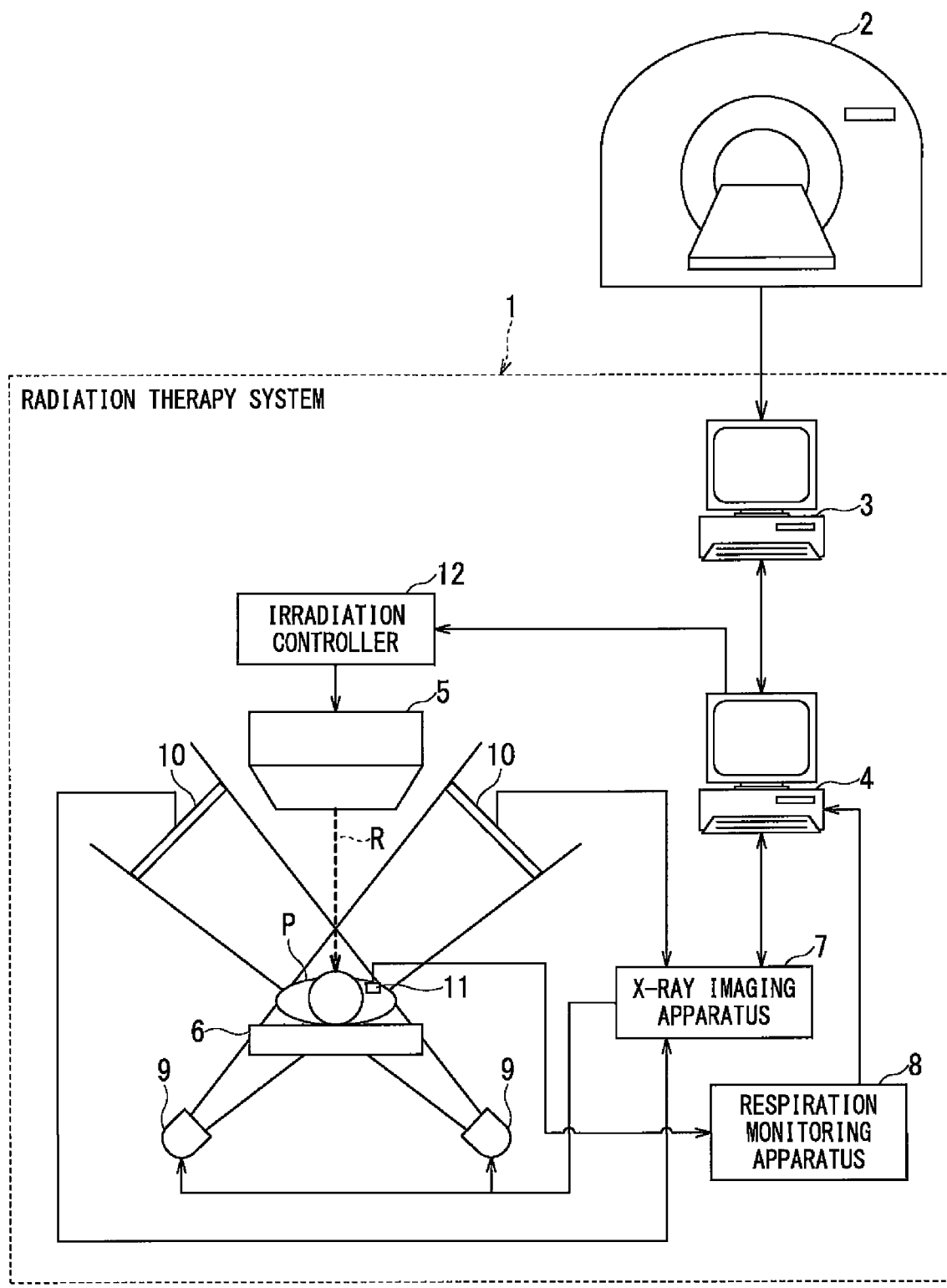
FIG. 1 is a system configuration diagram illustrating the radiation therapy system of the first embodiment.

In one embodiment of the present invention, a medical image processing apparatus comprising: a first input interface configured to acquire a three-dimensional volume image of an object which is provided with at least one marker, the three-dimensional volume image being generated by imaging the object using a medical examination apparatus; a second input interface configured to acquire geometry information of an imaging apparatus which is used for imaging the object to generate a fluoroscopic image of the object; and a specific-setting-information generator configured to generate specific setting information based on the three-dimensional volume image and the geometry information, the specific setting information being used for setting of imaging for generating an image depicting the at least one marker or setting of image processing of the image depicting the at least one marker.

First Embodiment

Hereinafter, embodiments will be described with reference to the accompanying drawings. First, the medical image processing apparatus of the first embodiment will be described with reference to FIG. 1 to FIG. 12. The reference sign 1 in FIG. 1 denotes a radiation therapy system used for radiotherapy, in which a lesion area T such as a tumor generated in a body of a patient P is irradiated with radioactive rays R. The radioactive rays R used for treatment include, e.g., X-rays, γ-rays, electron beams, proton beams, neutron beams, and heavy particle beams.

When radiotherapy is performed, the radioactive rays R with sufficient output must be accurately radiated onto the position of the lesion area T (i.e., target area) of the patient (object) P. Further, it is necessary to suppress exposure dose of normal tissues (non-target area) in the vicinity of the lesion area T. In the treatment of visceral cancer such as lung cancer, liver cancer, and pancreatic cancer, the lesion area T is always moving together with motion such as breathing, heartbeat, and intestinal motion. Among plural irradiation methods, in the gating irradiation method, the irradiation position and the irradiation range of the radioactive rays R are fixed in advance. Thus, it is necessary to grasp the movement of the lesion area T and to radiate the radioactive rays R at the timing when the lesion area T is at a specific position. In the tracking irradiation method, the position of the lesion area T is tracked and the radioactive rays R are radiated onto the lesion area T specified by the tracking processing. In the following, a description will be given of cases of the gating irradiation. However, the present invention can also be applied to the tracking irradiation method. For specifying the position of the lesion area T, for instance, an X-ray image is used. However, the lesion area T is not necessarily clearly depicted in the X-ray image.

For this reason, in the present embodiment, a marker M (FIG. 4) is placed in the vicinity of the lesion area T. This marker M appears more clearly than the lesion area T. Since this marker M moves synchronously with the movement of the lesion area T, the movement of the lesion area T is grasped by imaging and monitoring the movement of the marker M using X-rays. Afterward, the radioactive ray R are radiated at a timing when a predetermined irradiation condition is satisfied. For instance, the irradiation condition is such a timing that the patient P exhales (i.e., breathes out) and the marker M comes to a specific position, and the radioactive rays R are repeatedly radiated onto the lesion area T in synchronization with respiration of the patient P. Although radiation of the radioactive rays R in synchronization with respiration is exemplified in the following description, the radioactive rays R may be radiated in synchronization with other motion of the patient P such as heartbeat and intestinal motion.

Figure 4:
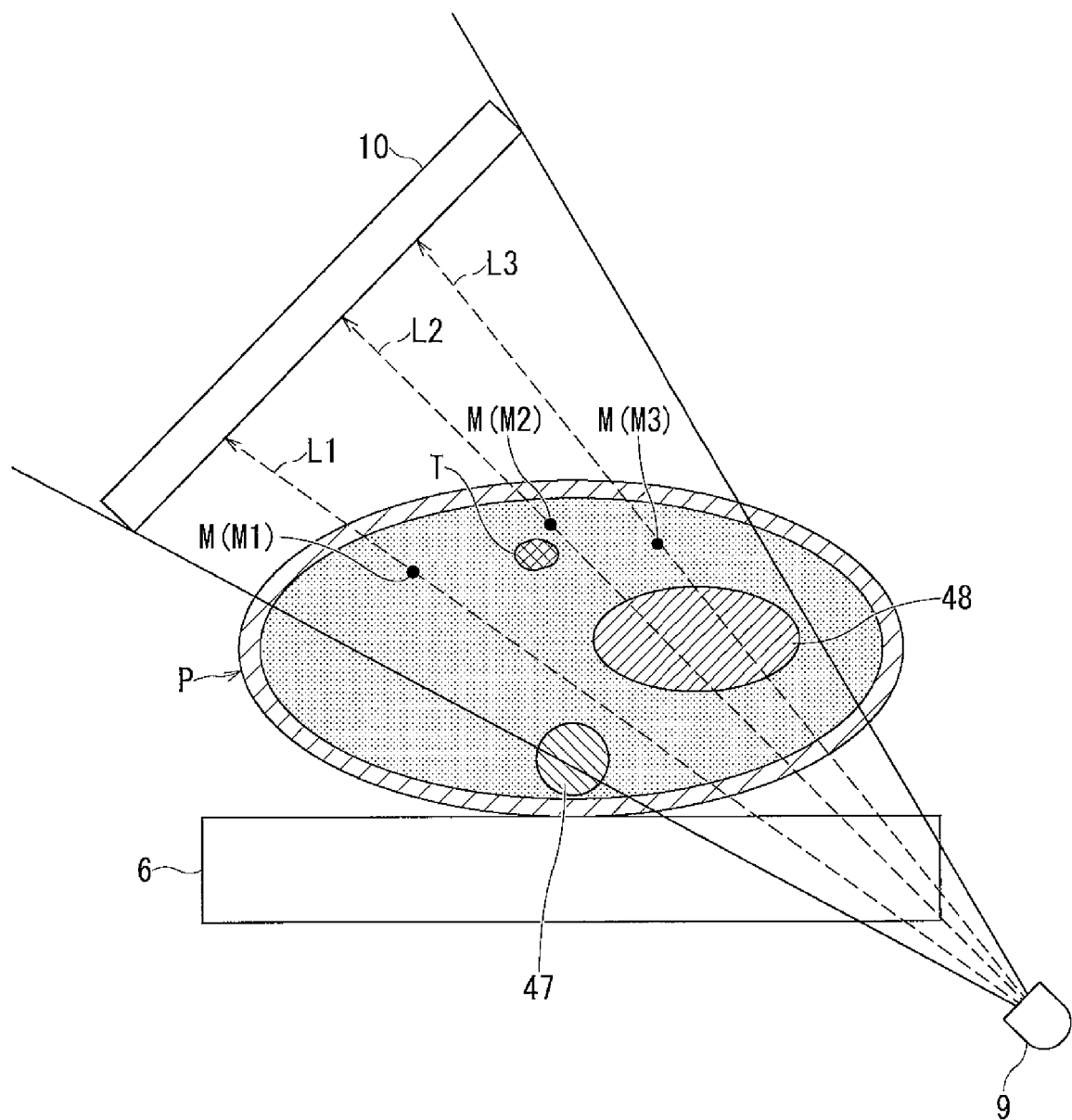
FIG. 4 is a schematic diagram illustrating relationship between X-ray irradiators, X-ray detectors, and a patient.

The marker M of the present embodiment is composed of, e.g., a minute metal ball having a diameter of approximately 1 to 2 mm. A material which is harmless even in the case of being placed or indwelled in the body is used as the material of the marker M. For instance, gold is used. Since metal is a material harder to transmit X-rays than tissues constituting a human body, metal is relatively clearly depicted in an X-ray image 40 (FIG. 5 to FIG. 8). In addition, the marker M is inserted into the body by using a dedicated puncture instrument such as an introducer (needle guide). For instance, plural markers M1 to M3 are placed in the vicinity of the lesion area T in the body (FIG. 4).

As shown in FIG. 1, in the case of preparing a treatment plan using the radiation therapy system 1, firstly, computed tomography is performed on the patient (object) P in which the marker M is placed. In the present embodiment, a medical examination apparatus 2 for performing various examinations of the patient P by computed tomography is provided. This medical examination apparatus 2 is configured as an X-ray CT (Computed Tomography) apparatus. A three-dimensional volume image of the patient P is generated by using the medical examination apparatus 2. The three-dimensional volume image is composed of, e.g., voxel data.

Although an X-ray CT apparatus is exemplified in the present embodiment, the medical examination apparatus (diagnostic apparatus) 2 may be another type of diagnostic apparatus as long as it can acquire a three-dimensional volume image of the patient P. For instance, the medical examination apparatus 2 may be configured as an MRI (Magnetic Resonance Imaging) apparatus or an ultrasonic diagnostic apparatus.

The radiation therapy system 1 of the present embodiment includes a medical image processing apparatus 3, an X-ray imaging apparatus 7 (i.e., fluoroscopic imaging apparatus), a respiration monitoring apparatus 8, a moving-object tracking apparatus 4, a radiation irradiation apparatus 5, and a bed 6 on which the patient P is placed. The medical image processing apparatus 3 generates specific setting information used for setting of imaging for generating an image depicting the marker M or setting of image processing of this image. The X-ray imaging apparatus 7 serially (i.e., sequentially) images the patient P so as to generate the X-ray images (fluoroscopic images) 40 in which the lesion area T of the patient P and the marker M are depicted. The respiration monitoring apparatus 8 monitors respiration of the patient P. The moving-object tracking apparatus 4 tracks (i.e., traces) the position of the marker M which moves every moment, by using the specific setting information and each X-ray image 40. The radiation irradiation apparatus 5 irradiates the lesion area T with radioactive rays when the marker M tracked by using the moving-object tracking apparatus 4 exists at a specific position (gating window) 41.

The medical image processing apparatus 3 and the moving-object tracking apparatus 4 of the present embodiment includes hardware resources such as a CPU (Central Processing Unit), a ROM (Read Only Memory), a RAM (Random Access Memory), and a HDD (Hard Disc Drive), and is configured as a computer in which information processing by software is achieved with the use of the hardware resources by causing the CPU to execute various programs.

Further, a medical image processing method of the present embodiment is achieved by causing the computer to execute the various programs.

In addition, the X-ray imaging apparatus 7 and the respiration monitoring apparatus 8 are connected to the moving-object tracking apparatus 4. In each of the X-ray images 40, an image of the marker M appears. Further, the moving-object tracking apparatus 4 tracks the position of the marker M in each X-ray image 40 generated by imaging the patient P with the use of the X-ray imaging apparatus 7 during radiotherapy, and monitors the respiratory state (e.g., breathing waveform) of the patient P by using the respiration monitoring apparatus 8. Moreover, the moving-object tracking apparatus 4 specifies the irradiation timing of the radioactive rays R, and outputs an irradiation timing signal.

The X-ray imaging apparatus 7 includes two X-ray irradiators 9 configured to irradiate the patient P with X-rays and two X-ray detectors 10 configured to detect X-rays transmitted through the patient P. Incidentally, each of the X-ray detectors 10 is composed of, e.g., a flat panel detector (FPD) or an image intensifier.

In other words, the radiation therapy system 1 of the present embodiment is provided with two pairs of X-ray irradiation and detection units, each of which includes one X-ray irradiator 9 and one X-ray detector 10. The three-dimensional position of the marker M can be specified by simultaneously performing X-ray imaging from two different directions with the use of the two pairs of the X-ray irradiators 9 and the X-ray detectors 10. In addition, it is possible to associate the same markers M, which are depicted in the respective X-ray images 40 generated by simultaneously imaging the patient P from the two directions, with each other by performing image processing.

In actual X-ray imaging, two pairs of the X-ray irradiators 9 and the X-ray detectors 10 are used for imaging the patient P from two directions (e.g., the direction from the right-hand side of the patient P and the direction the from left-hand side of the patient P) so as to generate a pair of X-ray images (medical images) 40. Further, as to a DRR image (Digitally Reconstructed Radiograph image, digital reconstructed radiograph, or medical image) 46 described below, a pair of images can be obtained. However, in the following description, the X-ray images 40 and the DRR images 46 taken from one direction will be exemplified in order to facilitate understanding of the embodiments (FIG. 5 to FIG. 8).

Figure 5:
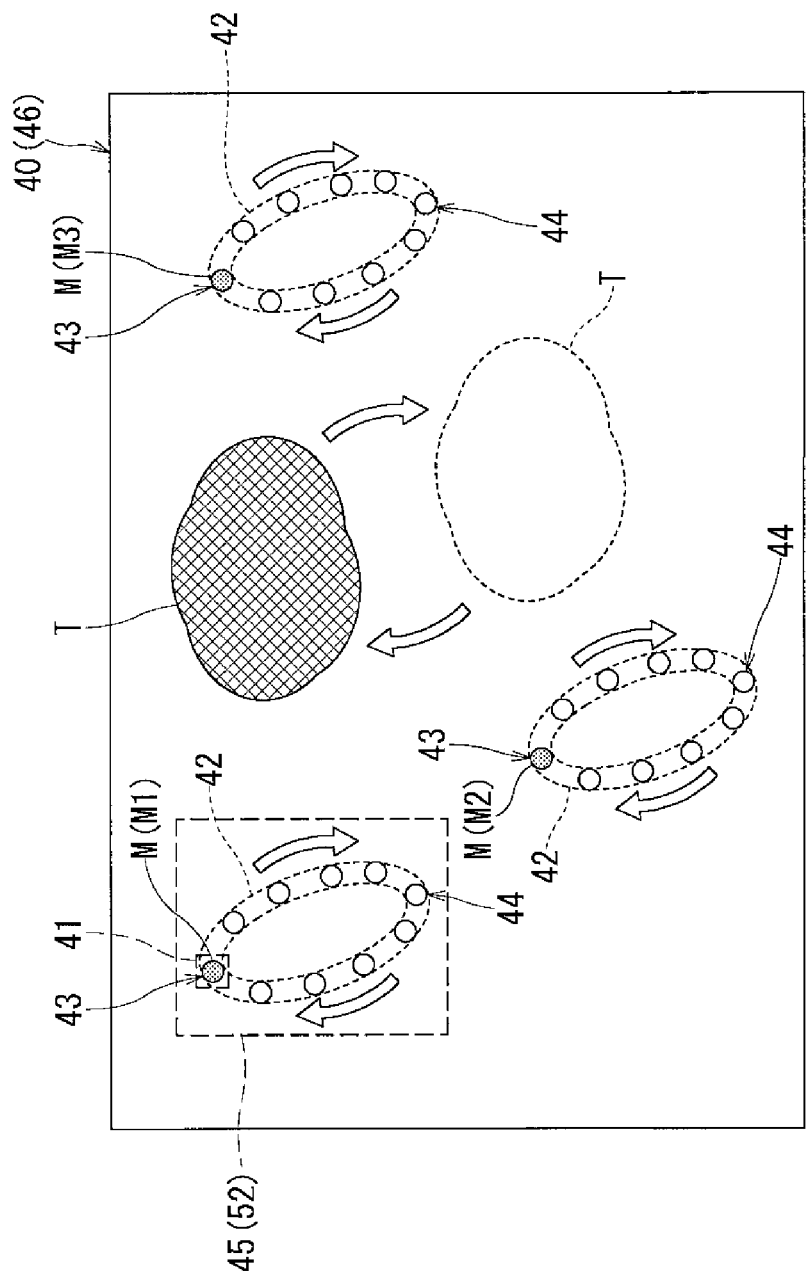
FIG. 5 is a schematic diagram illustrating an X-ray image (DRR image) used for tracking a marker.
Figure 6:
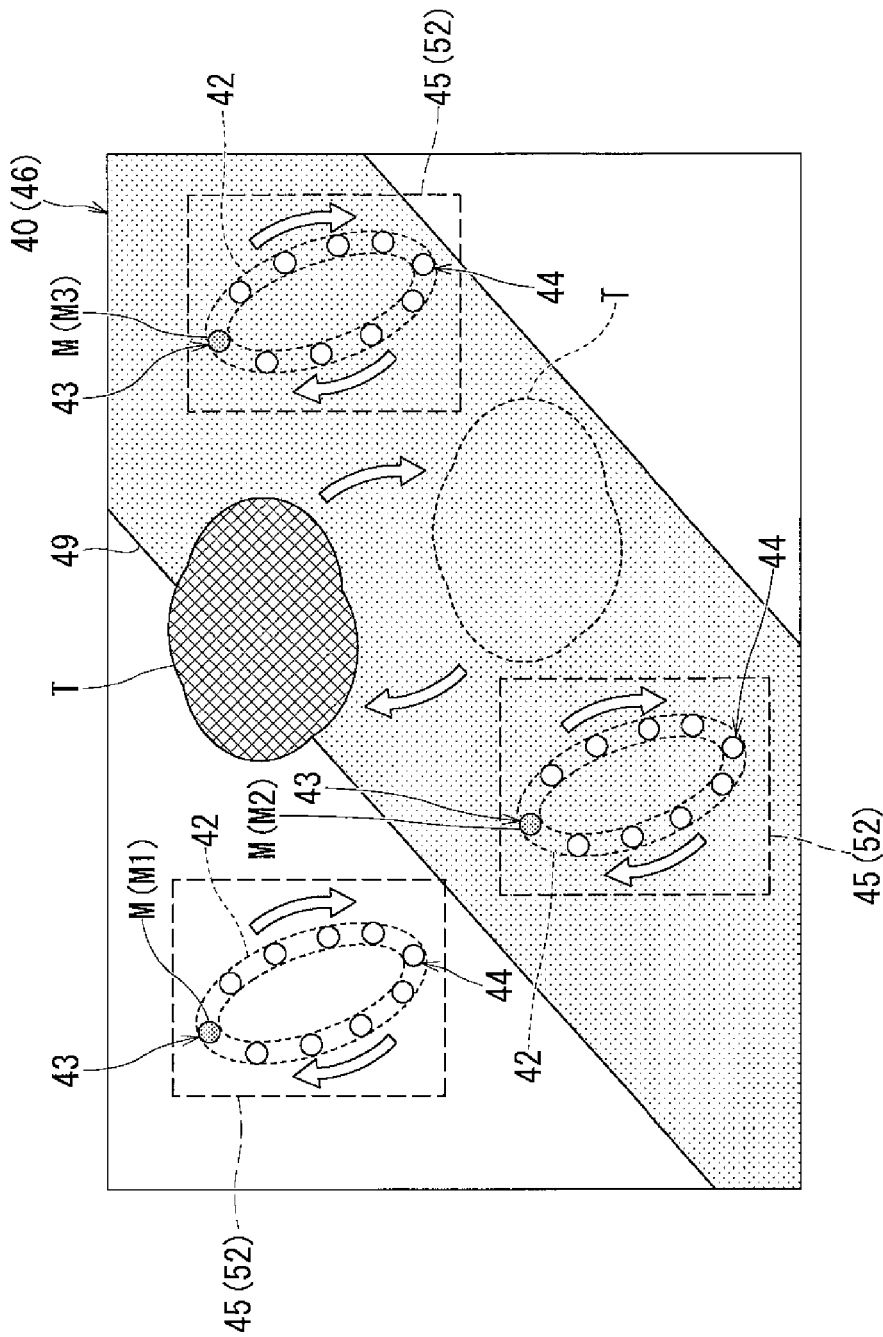
FIG. 6 is a schematic diagram illustrating an X-ray image (DRR image) used for selecting a marker.

As shown in FIG. 5, the lesion area T and plural markers M appear in the X-ray image 40. It is determined by the conditions of the X-ray irradiators 9 and the X-ray detectors 10 such as their arrangement and their orientation how the lesion area T and each marker M are depicted in the X-ray image 40. Since the X-ray images 40 are time-sequentially and continuously generated, it is possible to generate a moving image from the plural X-ray images (frames) 40. By performing image processing on the time-sequential X-ray images 40, it is possible to grasp the movement of the marker M, i.e., the motion of the lesion area T.

For instance, by connecting the position of the marker M of each of the plural X-ray images 40, it is possible to acquire the moving track 42 of the marker M. In the moving track 42 of the marker M, the end point position 43 at the time of exhaling (i.e., breathing out) and the end point position 44 at the time of inbreathing (i.e., inhaling) are clear. The end point position 43 at the time of exhaling is defined as the specific position 41. When the marker M is present at this specific position 41, the radioactive rays R are radiated onto the lesion area T. In this manner, it is possible to realize accurate respiratory synchronized irradiation on the basis of tracking processing of the marker M. Incidentally, the specific position 41 is a specific area (e.g., rectangular area) included in the X-ray image 40 as shown in FIG. 5.

When the entire range of the X-ray image 40 is to be processed on a real-time basis, the processing load of the CPU becomes high. Thus, in order to reduce the load of the image processing, a specific range (search range) 45, where there is a possibility that the marker M is depicted in the X-ray image 40, is set and image processing of searching only this specific range 45 is performed. In addition, it is possible to three-dimensionally acquire the position of the marker M and its moving track 42 by acquiring a pair of images generated by imaging the patient P in two directions as the X-ray images 40 (DRR images 46) and then specifying the specific range 45 and the specific position 41 for the pair of the X-ray images 40 (DRR images 46).

As shown in FIG. 1, the respiration monitoring apparatus 8 is connected to a respiration sensor 11 which is attached to the patient P. This respiration sensor 11 is used for monitoring the respiratory state of the patient P. The respiration monitoring apparatus 8 outputs respiratory information indicative of the respiratory state of the patient P to the moving-object tracking apparatus 4. In the present embodiment, the radiation therapy system 1 is configured to radiate the radioactive rays R onto the lesion area T when both of the following first and second conditions are satisfied. The first condition is that the respiratory state of the patient P acquired by the respiration monitoring apparatus 8 indicates that the patient P exhaled. The second condition is that the marker M exists at the specific position 41. It should be noted that the radioactive rays R may be radiated onto the lesion area T when the marker M exists at the specific position 41 regardless of the respiratory state of the patient P.

In addition, the radiation irradiation apparatus 5 is connected to an irradiation controller 12. The irradiation timing of the radioactive rays R is controlled by the irradiation controller 12. Further, the irradiation controller 12 is connected to the moving-object tracking apparatus 4. The irradiation controller 12 controls the radiation irradiation apparatus 5 in such a manner that the radiation irradiation apparatus 5 radiates the radioactive rays R when the irradiation controller 12 receives the irradiation timing signal outputted from the moving-object tracking apparatus 4.

Figure 2:
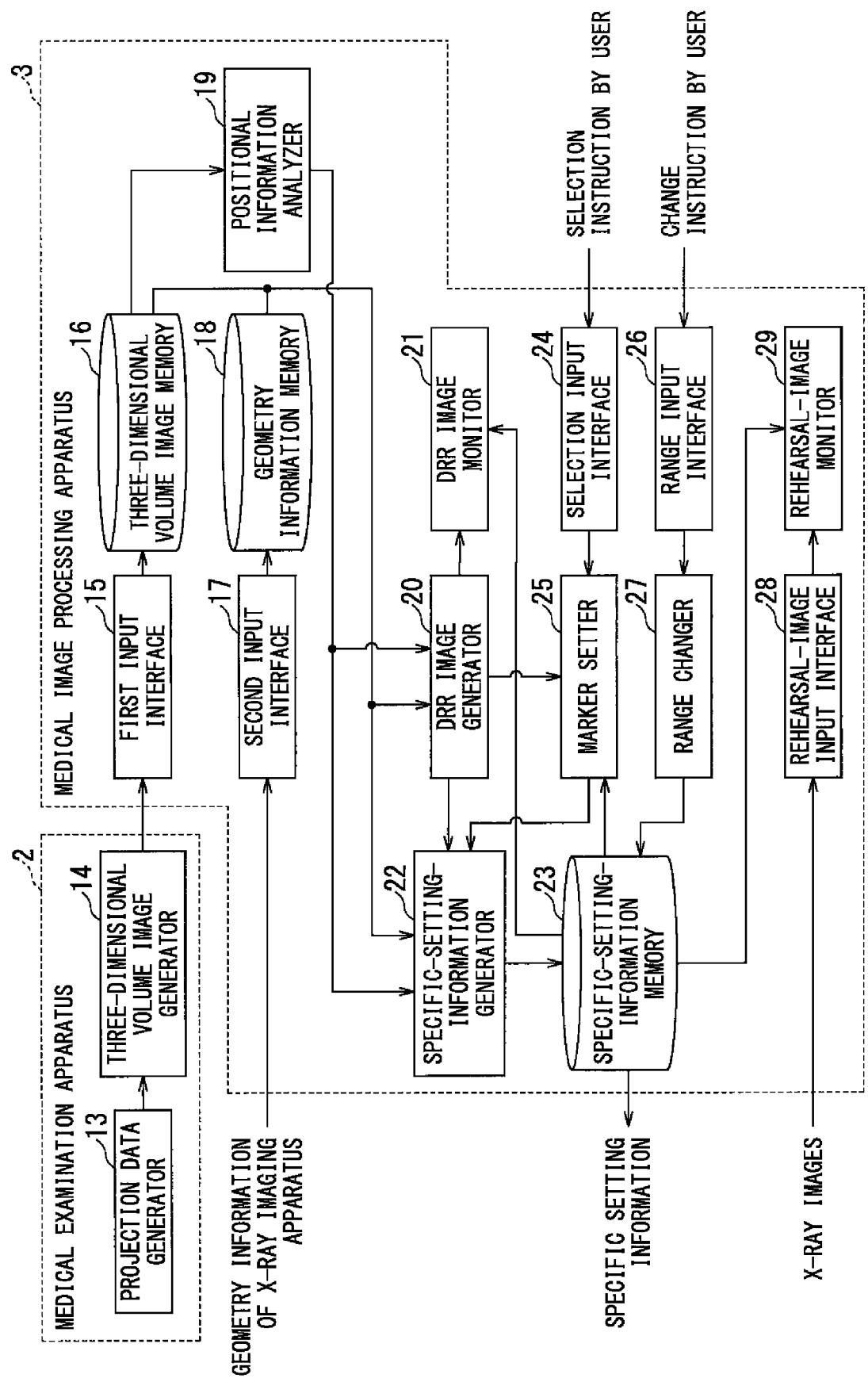
FIG. 2 is a block diagram illustrating the medical image processing apparatus of the first embodiment.

As shown in FIG. 2, the medical examination apparatus 2 is an apparatus for performing computed tomography of the patient P, and includes a projection data generator 13 configured to generate projection data of the patient P by imaging the patient P in plural directions and a three-dimensional volume image generator 14 configured to generate a stereoscopic and three-dimensional volume image of the patient P on the basis of plural two-dimensional projection data obtained by the projection data generator 13. The three-dimensional volume image includes, e.g., information of plural voxels. The three-dimensional volume image generator 14 outputs the three-dimensional volume image to the medical image processing apparatus 3. It is possible to generate a stereoscopic moving image of the patient P by time-sequentially and consecutively performing computed tomography. This makes it possible to acquire the three-dimensional movement of the lesion area T and the marker (s) M.

The medical image processing apparatus 3 includes a first input interface (i.e., first acquisition unit) 15, a three-dimensional volume image memory 16, a second input interface (i.e., second acquisition unit) 17, a geometry information memory 18, and a positional information analyzer (i.e., positional information acquisition unit) 19. The first input interface 15 acquires a three-dimensional volume image of the patient P from the medical examination apparatus 2. The three-dimensional volume image memory 16 stores the three-dimensional volume image acquired by first input interface 15. The second input interface 17 acquires geometry information of the X-ray irradiators 9 and the X-ray detectors 10 in the X-ray imaging apparatus 7 used for imaging the patient P to generate the X-ray images 40. The geometry information memory 18 stores the geometry information acquired by the second input interface 17. The positional information analyzer 19 acquires (i.e., calculates) positional information (e.g., coordinates) of the marker M on the basis of the three-dimensional volume image stored in the three-dimensional volume image memory 16.

Incidentally, the geometry information includes parameters indicating the positions of the respective X-ray irradiators 9, the positions of the respective X-ray detectors 10, and the orientation of the X-ray detection plane of each X-ray detector 10. The geometry information is preconfigured on the basis of, e.g., design drawing data (CAD data) of the X-ray imaging apparatus 7. Further, the second input interface 17 may store the geometry information in advance in addition to acquiring the geometry information from an external device. When the X-ray imaging apparatus 7 is movable, the second input interface 17 acquires and stores the geometry information in each state from the outside.

Moreover, the three-dimensional volume image of the patient P contains the CT value of the metal (e.g., gold) constituting the marker M. The positional information analyzer 19 can acquire the three-dimensional positional information of the marker M placed in the body of the patient P by specifying the CT value of the metal. Incidentally, the medical examination apparatus 2 time-sequentially and consecutively performs computed tomography. Accordingly, the respiratory state of the patient P is also time-sequentially monitored so as to correspond to the timing of each imaging (i.e., in synchronization with each imaging). The respiratory information indicative of the respiratory state is stored in the three-dimensional volume image memory 16 in association with the three-dimensional volume image obtained from the medical examination apparatus 2.

In addition, the three-dimensional volume image of the patient P includes the positional information of the lesion area T. Although the positional information of the lesion area T in the three-dimensional volume image is inputted by a user (e.g., a doctor) at the time of treatment planning, the positional information of the lesion area T may be automatically identified to assist the user. When the positional information of the lesion area T at a specific time is inputted by a user, the positional information of the lesion area T and the marker M at other times can be calculated by image registration and thus can be automatically acquired. The positional information of the marker M in the three-dimensional volume image can be automatically acquired from the CT value as described above.

The medical image processing apparatus 3 includes a DRR image generator 20 configured to generate the DRR images 46 on the basis of the three-dimensional volume image of the patient P and the geometry information of the X-ray imaging apparatus 7, and further includes a DRR image monitor (i.e., reconstructed-image display unit) 21 configured to display each DRR image 46. It should be noted that each DRR image 46 is a virtual X-ray image 40 obtained by virtually imaging a three-dimensional volume image with the use of the X-ray imaging apparatus 7. Since the X-ray image 40 and the DRR image 46 are images having almost the same composition, it is assumed in the following description that each of the four schematic image diagrams exemplified in FIG. 5 to FIG. 8 is the X-ray image 40 and is also the DRR image 46.

As shown in FIG. 2, the medical image processing apparatus 3 includes a specific-setting-information generator 22 and a specific-setting-information memory 23. The specific-setting-information generator 22 generates specific setting information on the basis of the three-dimensional volume image of the patient P, the geometry information of the X-ray imaging apparatus 7, the positional information of the marker M, and the DRR images 46. The specific setting information is used for setting of imaging for generating an image depicting the marker M or setting of image processing of this image. The specific-setting-information memory 23 stores the specific setting information. An image depicting the marker M (i.e., an image in which the marker M appears) includes both of the X-ray images 40 generated by the X-ray imaging apparatus 7 and the DRR images 46 generated by the DRR image generator 20.

The specific setting information (tracking condition) of the present embodiment relates to the setting used for generating the X-ray image 40 with the X-ray imaging apparatus 7 and for tracking the movement of the marker M with the moving-object tracking apparatus 4. For instance, the specific setting information includes information for predicting the moving track 42 of the marker M and setting the specific range 45 and the specific position 41 in the X-ray images 40 (FIG. 5). In addition, the specific setting information further includes information as to whether one of the plural markers M provided in the patient P is set as a target of image processing or not.

By generating the specific setting information in this manner, it is possible to automate the setting of the specific range 45 and the specific position 41 used for the image processing to be performed by the moving-object tracking apparatus 4. Thus, it is possible to save time and labor for a user such as a doctor or a radiological technician. Further, by generating the specific setting information with the use of the positional information of the marker M, it is possible to image an area including the marker M or perform image processing on an image in which the marker M is depicted depending on the position of the marker M.

It should be noted that the specific setting information can be generated in advance of imaging the patient P (i.e., generating the X-ray image 40). As compared with a case where it is required to image the patient P in advance to generate the X-ray image 40 because setting as to tracking the marker M is manually performed, the setting as to tracking the marker M can be completed in a shorter time in the present embodiment. Since it is not required to preliminarily image the patient P in the present embodiment, exposure dose to the patient can be reduced.

Since image processing can be performed mainly on the specific range 45 depicting the marker M by including the information for setting the specific range 45 in the specific setting information, the processing load can be reduced. Further, since the specific setting information includes information for setting the specific position 41 (gating window), it is possible to set a radiation irradiation timing of the radiation irradiation apparatus 5 by using the specific setting information. It should be noted that the specific position 41 may be a pinpoint or an area having a predetermined margin.

The specific setting information may be used for setting for improving the output of X-rays radiated onto a range where there is a high possibility that the marker M is present. By improving the irradiation output of X-rays to a range where there is a high possibility that the marker M is present as described above, the radiation therapy system 1 can clearly image the marker M in the X-ray image 40 while reducing the exposure dose of tissues other than the marker M. Accordingly, it is possible to more easily perform the image processing for specifying the marker M which is depicted in each X-ray image 40.

As shown in FIG. 4, there are parts which are hard to transmit X-rays such as a bone 47 and an internal organ 48 in the body of the patient P and/or metal parts of the bed 6. When the image of the marker M superimposes the image 49 of such a part (FIG. 6), it is difficult to specify the position of the marker M by image processing. For this reason, it is preferable that the specific-setting-information generator 22 generates the specific setting information used for specifying the marker M clearly depicted on the X-ray image 40 out of the plural markers M placed in the body of the patient P.

For instance, three markers M1 to M3 are placed in the body. In this case, the specific-setting-information generator 22 identifies the straight line L1 which extends from the X-ray irradiator 9 to the X-ray detector 10 so as to pass the position of the marker M1, the straight line L2 which extends from the X-ray irradiator 9 to the X-ray detector 10 so as to pass the position of the marker M2, and the straight line L3 which extends from the X-ray irradiator 9 to the X-ray detector 10 so as to pass the position of the marker M3.

Further, the specific-setting-information generator 22 virtually places a three-dimensional volume image between the X-ray irradiator 9 and the X-ray detector 10. When the three-dimensional volume image is a CT image, each voxel constituting the CT image is given a CT value indicative of difficulty of transmitting X-rays. A larger CT value is given to each voxel of a portion which is difficult to transmit X-rays such as the bone 47 and the internal organ 48 as compared with respective CT values of other voxels. For this reason, the specific-setting-information generator 22 calculates the total value of the CT values of all the voxels that are passing points of the straight line L1 in the virtual three-dimensional volume image existing between the X-ray irradiator 9 and the X-ray detector 10. The specific setting unit 22 calculates the total value of the CT values of all the voxels that are passing points of the straight line L2 in the virtual three-dimensional volume image, and similarly calculates the total value of the CT values of all the voxels that are passing points of the straight line L3 in the virtual three-dimensional volume image. The specific-setting-information generator 22 selects a straight line corresponding to the minimum total value of the three total values. In the case of FIG. 4, the straight line L1 is specified because it does not pass through the area of the internal organ 48 compared with the straight lines L1 and L2. Then, the marker M1 corresponding to the specified straight line L1 is set as a target of image processing. In this manner, the marker M1 suitable for the image processing can be selected from the plural markers M1 to M3.

When the three-dimensional volume image is a CT image, the specific-setting-information generator 22 of the present invention selects and sets the marker M1 as the target of image processing from the straight lines L1 to L3 passing through the respective positions of the markers M1 to M3. This is because the marker M1 corresponds to the straight line L1 having the smallest sum of the CT values of all the voxels existing on the straight line from the X-ray irradiator 9 to the X-ray detector 10. In this manner, when the patient P is imaged to generate the X-ray images 40, the marker M1 most clearly depicted in the X-ray images 40 can be selected from the plural markers M1 to M3. It should be noted that any one of the markers M1 to M3 may be subjected to the image processing. Additionally, two or more of the markers M1 to M3 may be subjected to the image processing. When two or more markers are set as the targets of the image processing, two straight lines may be specified in ascending order of the total value of the voxel values so that the specified two markers are targeted.

The marker M as the image processing target may be specified on the basis of the voxel values of the three-dimensional volume image as described above or may be specified on the basis of the evaluation of the contrast of each DRR image 46. Further, the marker M as the image processing target may be specified by using the evaluation of the voxel values of the three-dimensional volume image and the evaluation of the contrast of the DRR image 46 in combination.

When the specific-setting-information generator 22 evaluates the contrast of the DRR image 46, the specific-setting-information generator 22 specifies (i.e., selects) the one having the highest contrast with the surroundings from the respective images of the markers M1 to M3 depicted in the DRR image 46. Since it is only necessary to evaluate the contrast with the surroundings, it is not necessary to generate the entire DRR image 46. If only the partial images around the markers M1 to M3 are generated, the contrast with the surroundings can be calculated.

Figure 7:
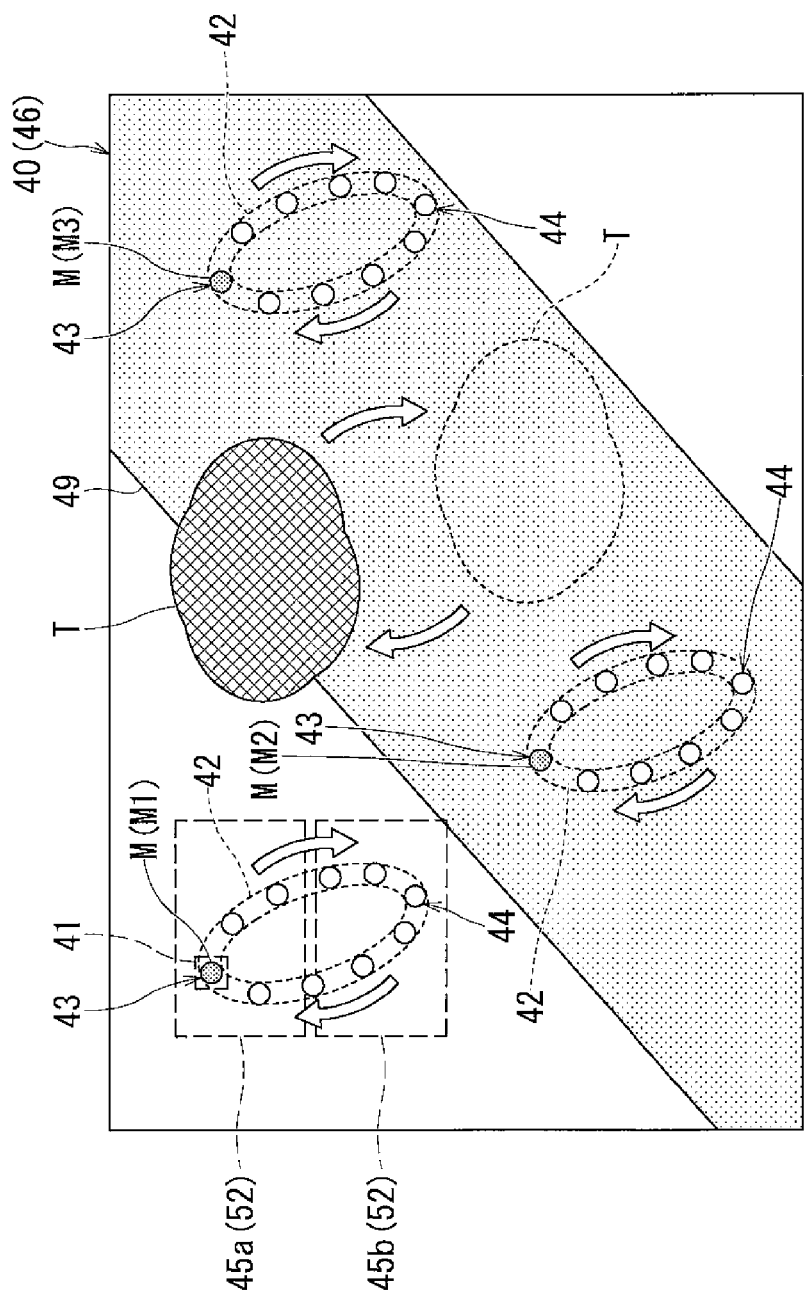
FIG. 7 is a schematic diagram illustrating an X-ray image (DRR image) when a range notification is changed.

Further, the specific setting information may include information for changing the specific range 45 according to the respiratory state of the patient P, which is acquired by using the respiration monitoring apparatus 8 for monitoring respiration of the patient P. For instance, when the patient P expands the volume of the lung by lowering the diaphragm and inhales, the marker M moves to the lower side of the X-ray image 40 as shown in FIG. 7. When the patient P narrows the volume of the lung by raising the diaphragm and exhales, the marker M moves to the upper side of the X-ray image 40. In this case, the specific range 45 may be changed in such a manner that only the upper side of the moving track 42 of the marker M is defined as the specific range 45*a* from the posterior half period of exhaling to the anterior half period of inhaling while only the lower side of the moving track 42 of the marker M is defined as the specific range 45*b* from the posterior half period of inhaling to the anterior half period of exhaling.

In this manner, the specific ranges 45*a* and 45*b* are set according to the respiratory state of the patient P, and it is possible to appropriately image the patient P for generating the X-ray images 40, in each of which the marker M is satisfactorily clearly depicted. In addition, since it is possible to set the specific ranges 45*a* and 45*b* of the minimum necessary area, load of the image processing can be reduced by narrowing the specific ranges 45*a* and 45*b*. Further, by using the specific ranges 45*a* and 45*b* in accordance with the respiration information outputted from the respiration monitoring apparatus 8, the risk of erroneously tracking noise as the marker M is more reduced. Although a description has been given of the case where two specific ranges are set depending on the respiratory state of the patient P, three or more specific ranges may be set. When three or more specific ranges are set, the load of tracking image processing can be further reduced.

Figure 8:
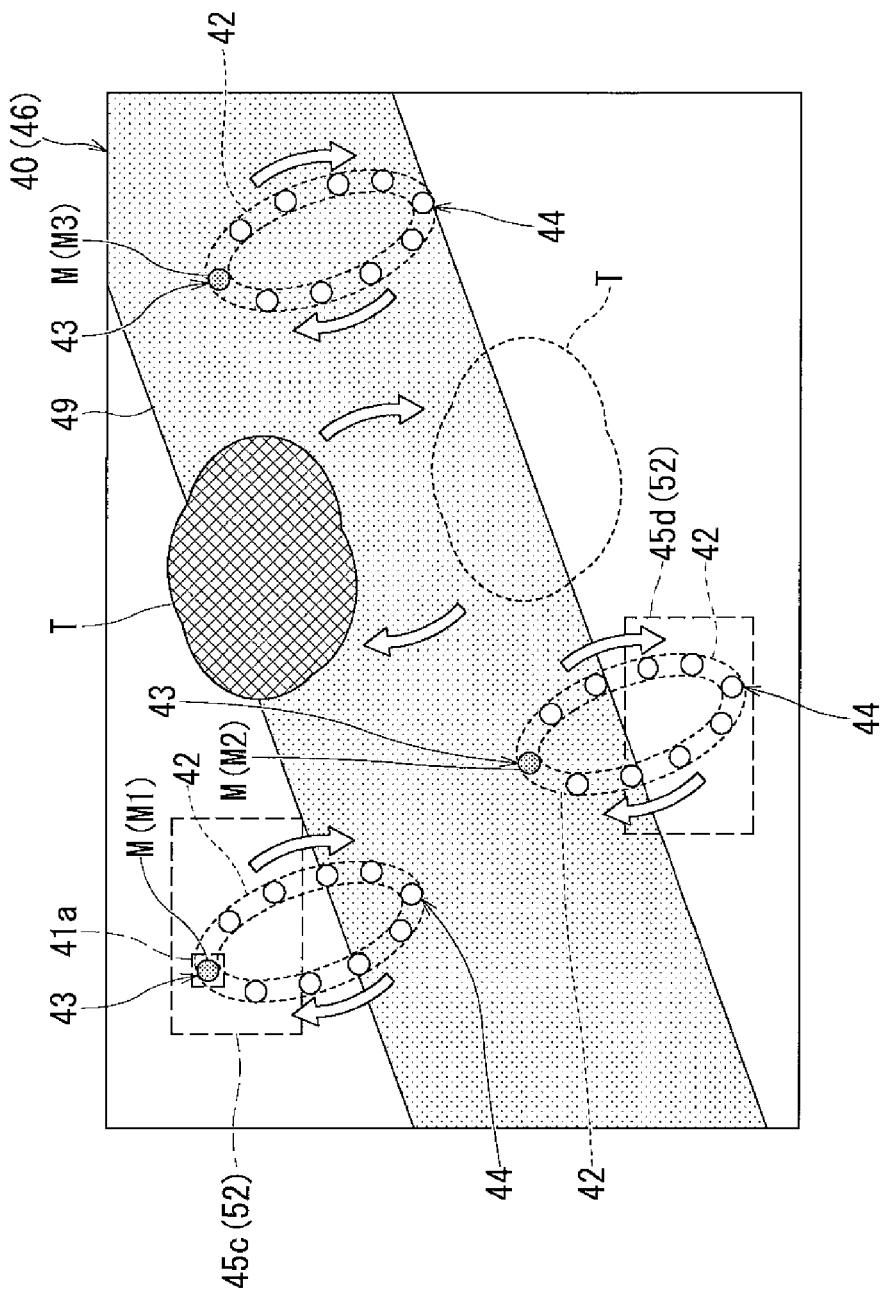
FIG. 8 is another schematic diagram illustrating an X-ray image (DRR image) when a range notification is changed.

Further, the plural markers M1 to M3 may be tracked in a complex manner by using the X-ray images 40. For instance, as shown in FIG. 8, a part of each of the moving tracks 42 of the plural markers M1 to M3 may be hidden in the image 49 of, e.g., the bone 47. In such a case, only the upper side of the moving track 42 of the predetermined marker M1 is defined as the specific range 45*c* from the posterior half period of exhaling to the anterior half period of inhaling and only the lower side of the moving track 42 of the other marker M2 is defined as the specific range 45*d* from the posterior half period of inhaling to the anterior half period of exhaling. The end point position 43 of the marker M2 at the time of exhaling is defined as a specific position 41*a*. In this manner, it is possible to track any marker M at any point in the breathing cycle.

A user such as a doctor or radiological technician can change the specific setting information while referring to the DRR images 46 or the X-ray images 40 of the patient P imaged by using the X-ray imaging apparatus 7 during rehearsal before treatment. For instance, a user can select the marker M to be tracked, change the specific ranges 45*c* and 45*d*, or change the specific position 41*a* in the moving-object tracking apparatus 4.

As shown in FIG. 2, the medical image processing apparatus 3 includes a selection input interface (i.e., selection-input reception unit) 24, a marker setter (i.e., marker setting unit) 25, a range input interface (i.e., range-input reception unit) 26, a range changer (i.e., range changing unit) 27, a rehearsal-image input interface (i.e., fluoroscopic-image acquisition unit) 28, and a rehearsal-image monitor (i.e., fluoroscopic-image display unit) 29. The selection input interface 24 receives a selection instruction of the marker M to be inputted by a user. The marker setter 25 sets the marker M, which is selected by the selection instruction, as a tracking target. The range input interface 26 receives a change instruction of the specific range 45 or the specific position 41 to be inputted by a user. The range changer 27 changes the specific setting information on the basis of the specific range 45 or the specific position 41 which corresponds to the change instruction. The rehearsal-image input interface 28 acquires the X-ray images 40 of the patient P imaged by using the X-ray imaging apparatus 7 (the moving-object tracking apparatus 4) during rehearsal before treatment. The rehearsal-image monitor 29 displays each X-ray image 40.

The above-described DRR image monitor 21 and the rehearsal-image monitor 29 may be configured as an integral monitor which switches between display of the DRR image 46 and display of the X-ray image 40 or displays both of the DRR image 46 and the X-ray image 40 in parallel (i.e., side by side in the vertical or horizontal direction). Further, each of the DRR image monitor 21 and the rehearsal-image monitor 29 may be configured as a separate monitor.

Further, the DRR image monitor 21 or the rehearsal-image monitor 29 sets the specific range 45 in the DRR image 46 or the X-ray image 40 on the basis of the specific setting information stored in the specific-setting-information memory 23. When displaying the DRR image 46 or the X-ray image 40, the DRR image monitor 21 or the rehearsal-image monitor 29 displays a range indication 52 indicative of the specific range 45 in such a manner that the range indication 52 is superimposed on the image (FIG. 5 to FIG. 8).

For instance, the range indication 52 is displayed so as to surround the moving track 42 of the marker M in the image. In this manner, a user can grasp the range, in which the marker M appears in the DRR image 46 or the X-ray image 40, by the range indication 52. Further, the medical image processing apparatus 3 may be configured to output or display the range indication 52 which is sufficient for a user to sufficiently understand related information such as the specific ranges 45a, 45b, 45c, and 45d.

Then, the selection input interface 24 receives an instruction to select the marker M inputted by the user. In addition, the marker setter 25 sends the received selection instruction to the specific-setting-information generator 22 such that the selection instruction is reflected on generation of the specific setting information. Further, the range input interface 26 receives a change instruction to change the specific range 45 or the specific position 41 inputted by the user. Moreover, the range changer 27 changes the specific setting information stored in the specific-setting-information memory 23 on the basis of the received change instruction. Incidentally, the selection input interface 24 and the range input interface 26 include a user interface (input unit) that can be operated by a user, such as a keyboard, a mouse, and a touch panel. The range input interface 26 does not need to receive a modification instruction from a user. For instance, the range input interface 26 may be an interface to which a modification instruction is inputted by an external program for determining whether the specific range 45 is correct or not.

Further, the marker setter 25 may automatically select the appropriate marker M from the plural markers M on the basis of the DRR image 46 generated by the DRR image generator 20. For instance, the marker M located closest to the lesion area T may be selected, or the marker M having a high contrast with the surroundings may be selected. Here, the marker setter 25 may select the appropriate marker M on the basis of the specific setting information stored in the specific-setting-information memory 23, or may newly select the appropriate marker M so as to send the information of the selected marker M to the specific-setting-information generator 22.

The medical image processing apparatus 3 may be configured such that a user can change the marker M automatically selected by the marker setter 25. For instance, when there are plural markers M, the marker setter 25 may surround the markers M as choices with the respective range indications 52 (FIG. 6) and select the range indication 52, which the user determined to be appropriate, from these range indications 52.

In this manner, the specific range 45 in which the marker M appears can be appropriately modified according to a user's decision. Further, while a user is watching the actual X-ray images 40 generated by imaging the patient P using the X-ray imaging apparatus 7 during rehearsal, the user can select the marker M, which is suitable for imaging the patient P to generate the X-ray image 40 or suitable for the image processing of the X-ray image 40, from the plural markers M.

Figure 3:
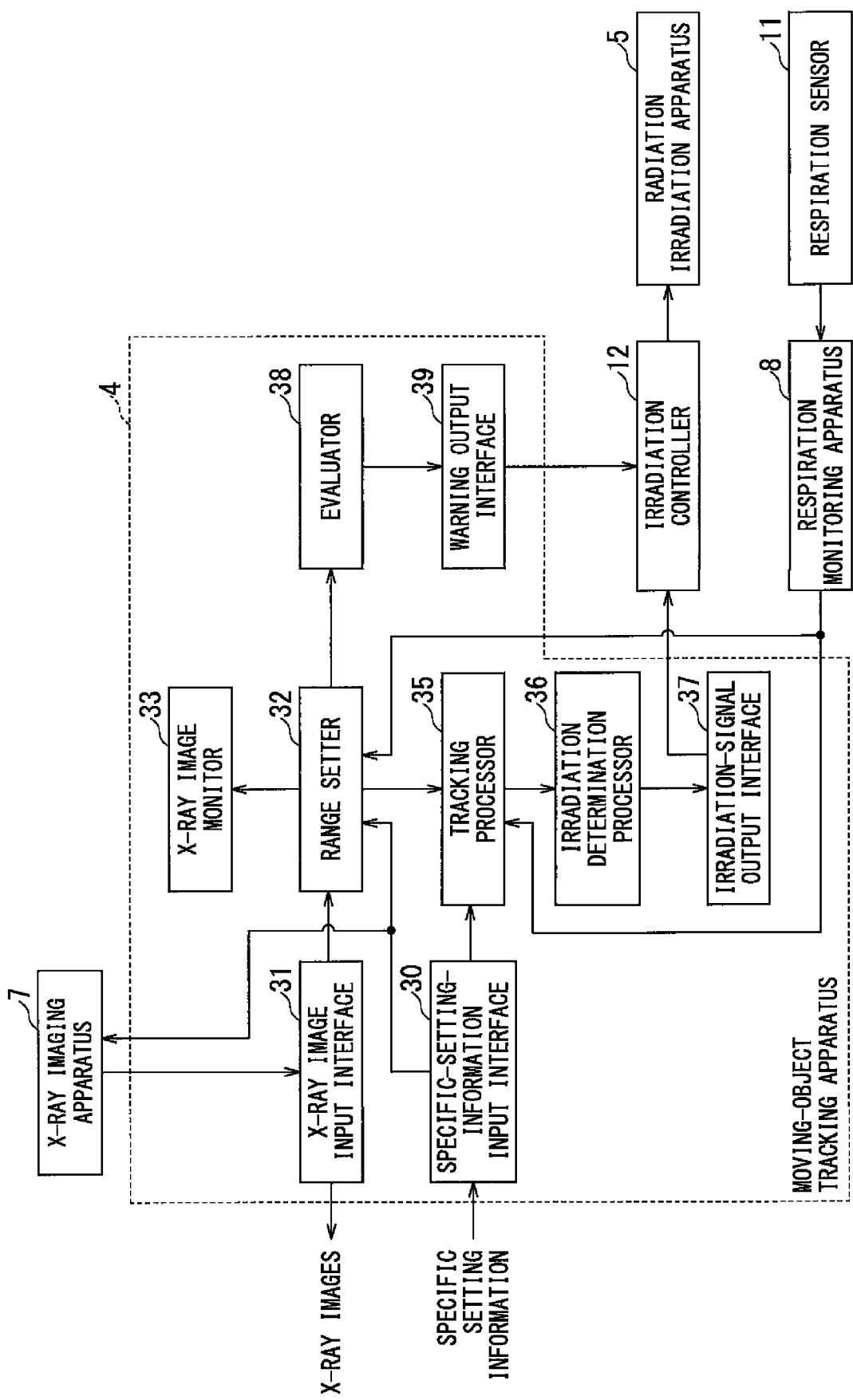
FIG. 3 is a block diagram illustrating the moving-object tracking apparatus of the first embodiment.

As shown in FIG. 3, the moving-object tracking apparatus 4 of the first embodiment includes a specific-setting-information input interface (i.e., specific-setting-information acquisition unit) 30, an X-ray image input interface (i.e., X-ray image acquisition unit) 31, a range setter (i.e., range setting unit) 32, and an X-ray image monitor (i.e., X-ray image display unit) 33. The specific-setting-information input interface 30 acquires the specific setting information from the medical image processing apparatus 3. The X-ray image input interface 31 acquires the X-ray images 40 generated by imaging the patient P with the use of the X-ray imaging apparatus 7. The range setter 32 sets the specific range 45 indicative of the range in which the marker M is depicted in the X-ray images 40, on the basis of the specific-setting-information. The X-ray image monitor displays the X-ray images 40.

Here, the specific setting information acquired by the specific-setting-information input interface 30 is inputted to the X-ray imaging apparatus 7. The X-ray imaging apparatus 7 uses the specific setting information for imaging the patient P so as to generate the X-ray image 40 in which the marker M appears. For instance, the X-ray imaging apparatus 7 sets the arrangement of the X-ray irradiators 9 and the X-ray detectors 10 on the basis of the specific setting information. In accordance with this setting, the X-ray irradiators 9 and the X-ray detectors 10 operate, and then X-ray imaging during rehearsal and X-ray imaging at the time of treatment are performed. Further, on the basis of the specific setting information, the X-ray imaging apparatus 7 may increase output of X-rays radiated onto the range where there is a high possibility that the marker M exists. Additionally or alternatively, the X-ray imaging apparatus 7 may reduce output of X-rays radiated onto the range where there is a high possibility that the marker M does not exist.

Note that the X-ray image 40 generated by the X-ray imaging apparatus 7 at the time of rehearsal before treatment is outputted to the medical image processing apparatus 3. In addition, each X-ray image 40 generated by the X-ray imaging apparatus 7 during treatment is displayed on the X-ray image monitor 33. When displaying the X-ray image 40, the X-ray image monitor 33 superimposes the range indication 52 indicative of the specific range 45 on the X-ray image 40 (FIG. 5 to FIG. 8).

Further, the moving-object tracking apparatus 4 includes a tracking processor (i.e., tracking unit) 35, an irradiation determination processor (i.e., irradiation determination unit) 36, and an irradiation-signal output interface (i.e., irradiation-signal output unit) 37. The tracking processor 35 performs image processing of tracking the position of the marker M appearing in the X-ray images 40 by using the specific setting information. The irradiation determination processor 36 determines whether it is the irradiation timing of radioactive rays R or not, on the basis of the position of the marker M. The irradiation-signal output interface 37 outputs the irradiation timing signal when it is determined to be the irradiation timing by the irradiation determination processor 36.

Here, the moving-object tracking apparatus 4 tracks the marker M appearing in the X-ray images 40 by using the tracking processor 35. When the marker M exists at the specific position 41, i.e., when the irradiation determination processor 36 determines that it is the irradiation timing of the radioactive rays R, the irradiation-signal output interface 37 outputs the irradiation timing signal to the irradiation controller 12. When receiving the irradiation timing signal outputted from the moving-object tracking apparatus 4, the irradiation controller 12 causes the radiation irradiation apparatus 5 to radiate radioactive rays R.

The moving-object tracking apparatus 4 further includes an evaluator (i.e., evaluation unit) 38 and a warning output interface (i.e., warning output unit) 39. The evaluator 38 evaluates magnitude relationship between a predetermined threshold value and a gray value of each pixel/voxel of the area of the marker M positionally detected in the X-ray image 40. The warning output interface 39 outputs a warning signal when there is a possibility that the detection of the marker M using the tracking processor 35 has failed.

The tracking processor 35 detects the marker M by performing image processing of the specific range 45 of the X-ray images 40. Various techniques can be applied to this image processing. In a part of this image processing, the tracking processor 35 performs processing of detecting the marker M appearing in the X-ray images 40 on the basis of the gray value of each pixel in the specific range 45 in the present embodiment. For instance, when there is a circular image in the specific range 45 and the circular image is darker than the surroundings, it is estimated that the spherical marker M is depicted as a circular image.

In the present embodiment, it is assumed that each portion which is hard to transmit X-rays is darkly depicted on the X-ray images 40, such as the marker M. Further, in each X-ray image, a gray value of a pixel of a bright part is large and a gray value of a pixel of a dark part is small. In addition, the X-ray image 40 can be reversed in black and white. In the case of reversing black and white from the above-described pixel-value aspect, a portion which is hard to transmit X-rays appears relatively bright on each X-ray image 40. Thus, the terms "bright" and "dark" and magnitude of a gray value described in the following description can be arbitrarily changed according to the black and white reversal of the X-ray image 40.

Since various portions such as the internal organs of the patient P are depicted in the X-ray image 40, the marker M may be erroneously detected in some cases. When radiation irradiation is performed in such a state that a tracking failure occurs, there is a possibility that radiation irradiation cannot be performed on an appropriate position of the patient P.

Thus, the evaluator 38 of the present embodiment evaluates the gray value of each pixel in the specific range 45 on the basis of a preset threshold value. Since the marker M is harder to transmit X-rays than body tissues, in the entire X-ray image, the gray value of the image portion of the marker M is significantly different from the image portion of the surrounding living tissues or an image portion generated by noise. Accordingly, for instance, the threshold value is previously set to a value which is indicative of being relatively bright among possible gray values used for each pixel of the marker M. Then, the evaluator 38 evaluates whether the gray value of the position detected as the marker M in the X-ray image 40 is larger or smaller than the threshold value. When the evaluated gray value is larger than the threshold value, the evaluated gray value is too bright for the marker M and there is a high possibility that the tracking processor 35 has erroneously detected, as the marker M, the position where the marker M is not depicted.

Further, depending on the magnitude relation evaluated by the evaluator 38, the warning output interface 39 outputs the warning signal to the irradiation controller 12. The warning signal may be outputted only when the gray value of the detection position is larger than the threshold value. In addition, the moving-object tracking apparatus 4 may perform notification of warning by display or voice together with output of the warning signal. By performing notification of warning, a user notices the risk and can quickly interrupt the treatment. Further, a history of warnings may be stored.

In this manner, when there is a possibility that detection of the marker M has failed, i.e., when there is a possibility that radiation irradiation cannot be performed on an appropriate position of the patient P, the warning can be outputted. When the irradiation controller 12 receives the warning signal regardless of receiving the above-described irradiation timing signal, the irradiation controller 12 controls the radiation irradiation apparatus 5 such that irradiation of radioactive rays R is not performed.

In other words, the moving-object tracking apparatus 4 of the present invention includes (a) the range setter 32 for setting the specific range 45 indicative of the range in which the marker M appears in the X-ray images 40 by using the specific setting information and (b) the evaluator 38 for evaluating the magnitude relationship of the gray value of the position detected as the marker M with respect to the predetermined threshold value, and the warning output interface 39 outputs the warning signal when the gray value of the detection position is larger than the threshold value. In this manner, it is possible to quantitatively evaluate the presence/absence of the possibility that the detection of the marker M has failed, on the basis of the predetermined threshold value.

Although the warning signal is outputted to the irradiation controller 12 in the present embodiment, it is not necessarily required to output the warning signal to the outside of the moving-object tracking apparatus 4. For instance, the warning signal may be inputted to the irradiation-signal output interface 37. The moving-object tracking apparatus 4 may be configured such that the irradiation timing signal is not outputted from the irradiation-signal output interface 37 in the case of outputting the warning signal.

The radiation irradiation apparatus 5 of the present embodiment radiates radioactive rays R onto the lesion area T when the marker M tracked by the moving-object tracking apparatus 4 exists at the specific position 41. By tracking the marker M in this manner, it is possible to grasp the movement of the lesion area T and radiate the radioactive rays R when the lesion area T is at an appropriate position.

Figure 9:
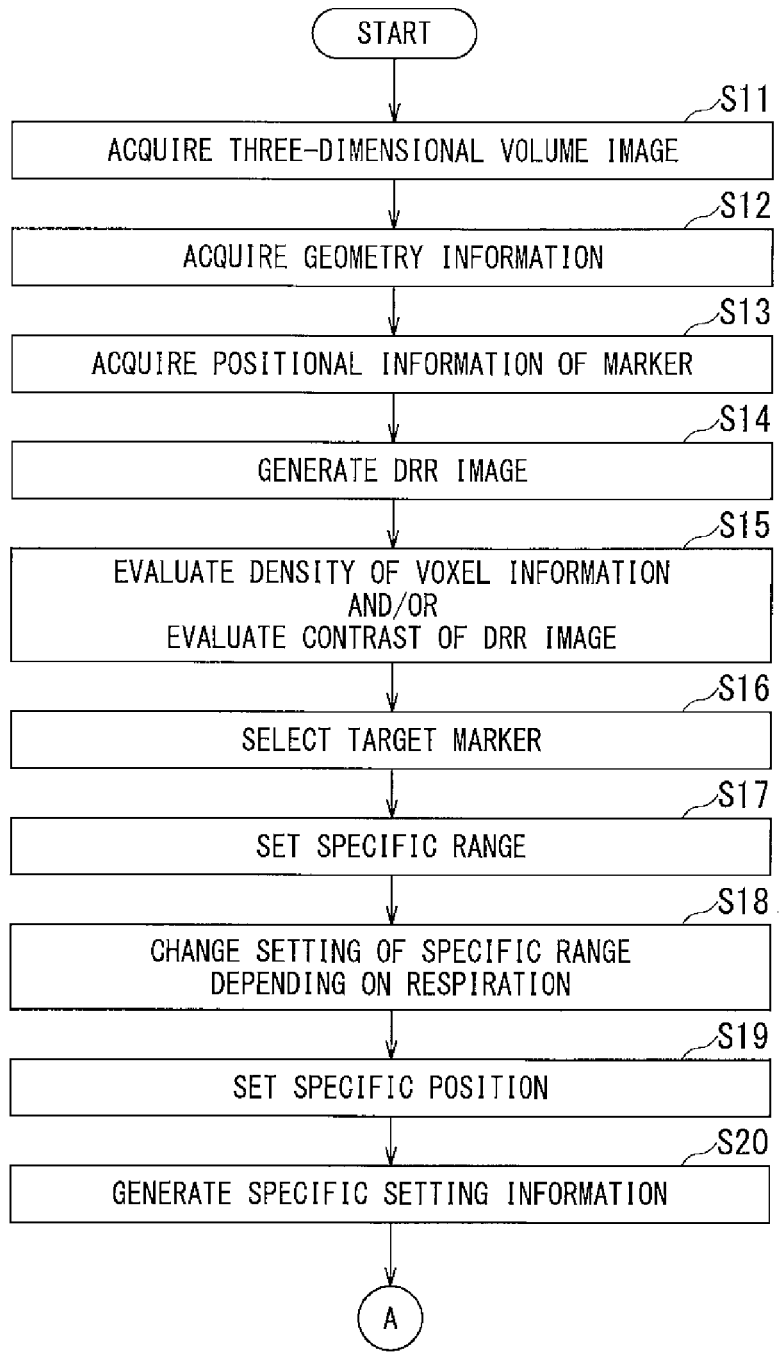
FIG. 9 is a flowchart illustrating the anterior part of the specific-setting-information generation processing to be performed by the medical image processing apparatus.
Figure 10:
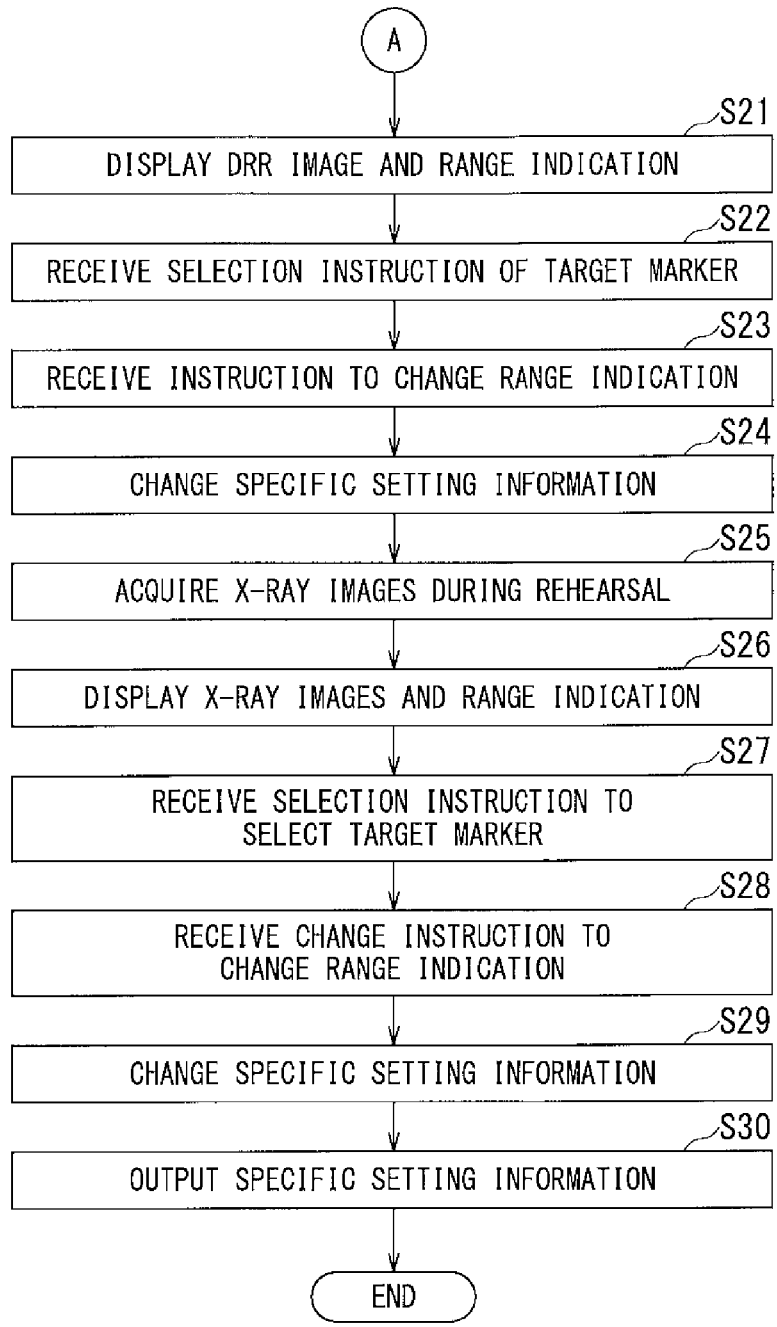
FIG. 10 is a flowchart illustrating the posterior part of the specific-setting-information generation processing to be performed by the medical image processing apparatus.

Next, a description will be given of the specific-setting-information generation processing (medical image processing method) executed by the medical image processing apparatus 3 with reference to FIG. 9 and FIG. 10. Although the image processing described below includes processing of moving images, processing of still images will be exemplified below in order to facilitate understanding of the specific-setting-information generation processing.

First, in the case of preparing a treatment plan, a three-dimensional volume image of the patient P is generated by examining (i.e., imaging) the patient P in which the marker M is placed with the use of the medical examination apparatus 2.

In the step S11 (i.e., the first acquisition step), the first input interface 15 of the medical image processing apparatus 3 acquires the three-dimensional volume image from the medical examination apparatus 2.

In the next step S12 (i.e., the second acquisition step), the second input interface 17 acquires the geometry information of the X-ray irradiators 9 and the X-ray detectors 10 in the X-ray imaging apparatus 7.

In the next step S13, the positional information analyzer 19 acquires three-dimensional positional information of the marker M placed in the body of the patient P on the basis of the value of each voxel constituting the three-dimensional volume image.

In the next step S14, the DRR image generator 20 generates the DRR image 46 on the basis of the three-dimensional volume image of the patient P and the geometry information of the X-ray imaging apparatus 7.

In the next step S15, the specific-setting-information generator 22 evaluates the value of each voxel constituting the three-dimensional volume image and/or the contrast of the image portion of the marker M depicted in the DRR image 46.

In the next step S16, depending on the evaluation result, the specific-setting-information generator 22 selects the marker expected to be depicted with the highest contrast in the X-ray image 40 from among the markers M1 to M3, as the target of image processing performed by the moving-object tracking apparatus 4.

In the next step S17, the specific-setting-information generator 22 performs setting of the specific range 45 (FIG. 5) of each of the X-ray images 40 and the DRR image 46.

In the next step S18, the specific-setting-information generator 22 changes the setting of the specific range 45 when the specific range 45 is changed depending on respiration of the patient P (FIG. 7 and FIG. 8).

In the next step S19, the specific-setting-information generator 22 performs setting of the specific position 41 of each of the X-ray images 40 and the DRR image 46.

In the next step S20 (i.e., the specific-setting-information generation step), the specific-setting-information generator 22 generates the specific setting information which includes various settings.

In the next step S21, the DRR image monitor 21 displays the DRR image 46 and the range indication 52 of the specific range 45. When there are plural choices for the marker M to be tracked, the range indications 52 corresponding to the respective markers M are displayed.

In the next step S22, the selection input interface 24 receives the selection instruction of the marker M inputted by a user at the time of treatment planning.

In the next step S23, the range input interface 26 receives the change instruction to change the specific range 45 or the specific position 41 inputted by a user.

In the next step S24, the marker setter 25 sends the received change instruction to the specific-setting-information generator 22 so as to reflect the change instruction in generation of the specific setting information, and the range changer 27 changes the specific setting information stored in the specific-setting-information memory 23 on the basis of the received change instruction.

In the next step S25, the rehearsal-image input interface 28 acquires the X-ray image 40 of the patient P generated by using the X-ray imaging apparatus 7 (the moving-object tracking apparatus 4) during rehearsal before treatment.

In the next step S26, the rehearsal-image monitor 29 displays the X-ray image 40 and the range indication 52 of the specific range 45. When there are plural choices for the marker M to be tracked, the range indications 52 corresponding to the respective markers M are displayed.

In the next step S27, the selection input interface 24 receives the selection instruction to select the marker M to be inputted by a user during rehearsal before treatment.

In the next step S28, the range input interface 26 receives the change instruction to change the specific range 45 or the specific position 41 to be inputted by a user.

In the next step S29, the marker setter 25 sends the received selection instruction to the specific-setting-information generator 22 so as to reflect the received selection instruction in generation of the specific setting information, and the range changer 27 changes the specific setting information stored in the specific-setting-information memory 23 on the basis of the received change instruction.

In the next step S30, the medical image processing apparatus 3 outputs the generated specific setting information to the moving-object tracking apparatus 4. As to the output of the specific setting information, the specific setting information may be outputted to the moving-object tracking apparatus 4 via a network or may be outputted to the moving-object tracking apparatus 4 after outputting the specific setting information to a storage medium. It is possible that the medical image processing apparatus 3 and the moving-object tracking apparatus 4 are integrally configured as one personal computer. Afterward, the medical image processing apparatus 3 completes the specific-setting-information generation processing.

Figure 11:
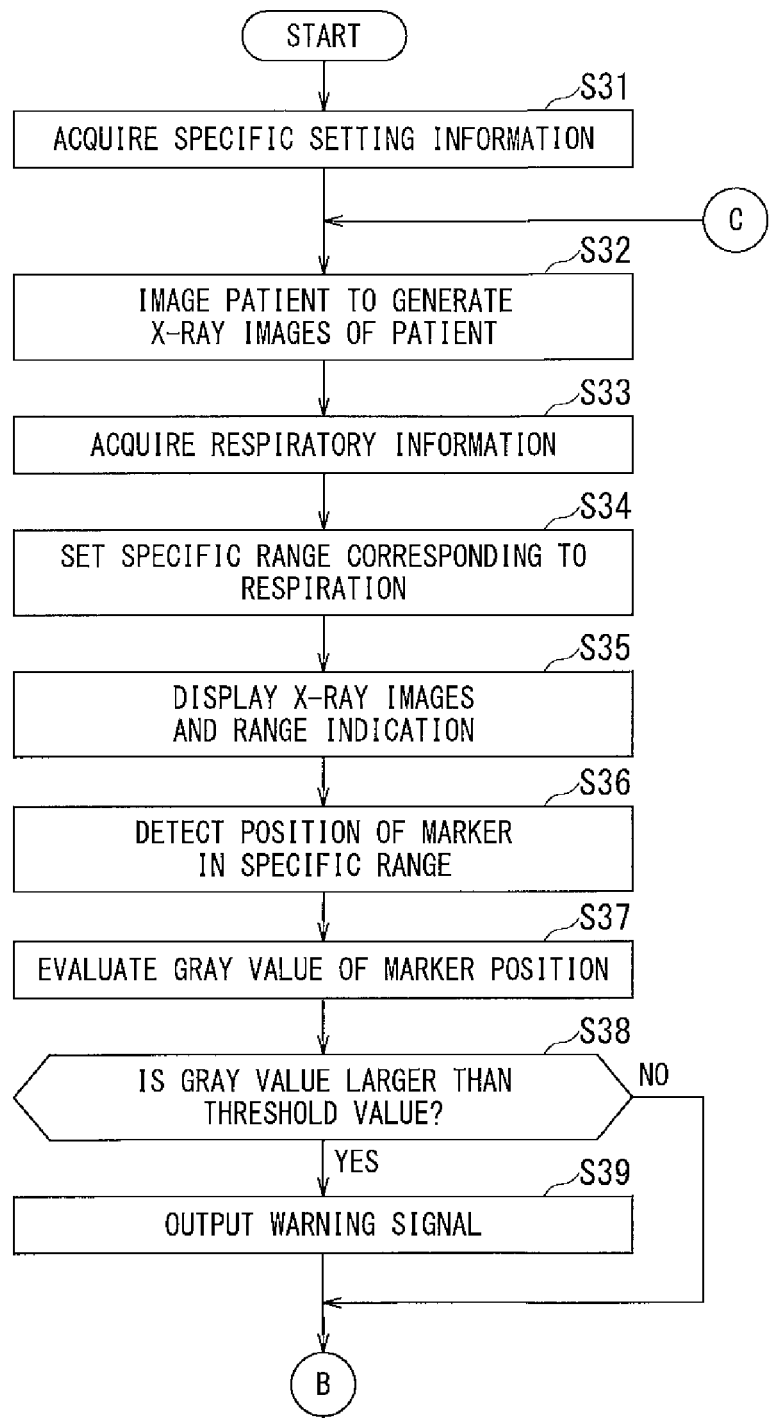
FIG. 11 is a flowchart illustrating the anterior part of the marker tracking processing to be performed by the moving-object tracking apparatus of the first embodiment.
Figure 12:
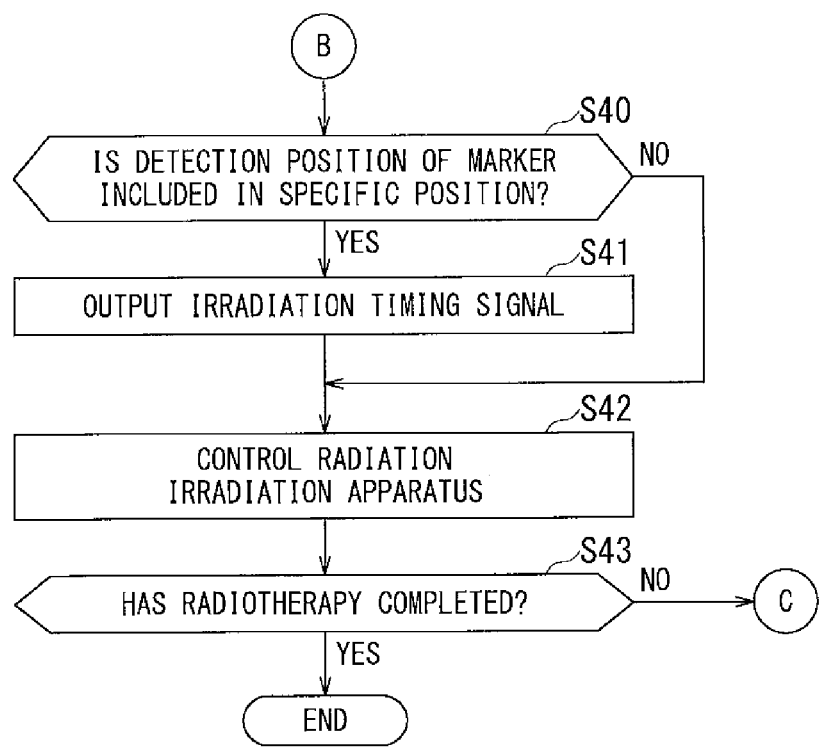
FIG. 12 is a flowchart illustrating the posterior part of the marker tracking processing to be performed by the moving-object tracking apparatus of the first embodiment.

Next, a description will be given of the marker tracking processing (medical image processing method) executed by the moving-object tracking apparatus 4 with reference to FIG. 11 and FIG. 12.

First, in the step S31, the specific-setting-information input interface 30 of the moving-object tracking apparatus 4 acquires the specific setting information from the medical image processing apparatus 3.

In the next step S32, radiotherapy is started. Specifically, the X-ray imaging apparatus 7 images the patient P so as to generate the X-ray images 40 of the patient P, and then the X-ray image input interface 31 acquires the X-ray images 40 from the X-ray imaging apparatus 7.

In the next step S33, the tracking processor 35 and the range setter 32 acquire respiratory information corresponding to the imaging time of each of the X-ray images 40 of the patient P from the respiration monitoring apparatus 8.

In the next step S34, the range setter 32 sets the specific range 45 in the X-ray images 40 on the basis of the specific setting information. When the specific range 45 is changed depending on or in response to the respiration of the patient P (FIG. 7 and FIG. 8), the range setter 32 sets the specific range 45 corresponding to the respiration of the patient P on the basis of the respiratory information inputted from the respiration monitoring apparatus 8.

In the next step S35, the X-ray image monitor 33 displays the X-ray image 40 and the range indication 52 of the specific range 45.

In the next step S36, the tracking processor 35 detects the position of the marker M from the specific range 45 in the X-ray image 40.

In the next step S37, the evaluator 38 starts the process of evaluating the magnitude relationship between the threshold value and the gray value of the position where the marker M is detected. In other words, the evaluator 38 starts the process of detecting the gray value of each pixel in the specific range 45.

In the next step S38, the evaluator 38 determines whether the gray value of the position where the marker M is detected is larger than the threshold value or not. When the gray value of the position where the marker M is detected is larger than the threshold value (i.e., when the position where the marker M is detected is bright), the processing proceeds to the step S39 in which the warning output interface 39 outputs the warning signal to the irradiation controller 12, and then the processing proceeds to the step S40. Conversely, when the gray value of the position where the marker M is detected is smaller than the threshold value (i.e., when the position where the marker M is detected is dark), the warning signal is not outputted and the processing proceeds to the step S40.

In the step S40, the irradiation determination processor 36 determines whether the position where the marker M is detected is included in the specific position 41 or not (FIG. 5). When the position where the marker M is detected is included in the specific position 41, the processing proceeds to the step S41 in which the irradiation-signal output interface 37 outputs the irradiation timing signal to the irradiation controller 12 and then the processing proceeds to the step S42. Conversely, when the position where the marker M is detected is not included in the specific position 41, the irradiation timing signal is not outputted and the processing proceeds to the step S42.

In the step S42, when the irradiation timing signal is inputted and the warning signal is not inputted, the irradiation controller 12 controls respective components in such a manner that the radioactive rays R are radiated by using the radiation irradiation apparatus 5. Otherwise, the irradiation controller 12 controls respective components in such a manner that irradiation of the radioactive rays R is not performed. Thereafter, the processing proceeds to the step S43.

In the step S43, the moving-object tracking apparatus 4 determines whether the radiotherapy has completed or not. The termination condition of the radiotherapy is determined in the treatment plan in advance. When the radiotherapy has not been completed, the processing returns to the step S32 as described above. Conversely, when the radiotherapy is completed, the marker tracking process is completed.

In the present invention, setting of imaging a patient for generating an image in which the marker is depicted or setting of image processing of this image includes setting of fluoroscopic imaging for generating fluoroscopic images, setting of generation of a digital reconstructed radiograph (setting of imaging in a virtual space), setting of image processing of fluoroscopic images, and setting of image processing of the digital reconstructed radiographs.

Second Embodiment

Figure 14:
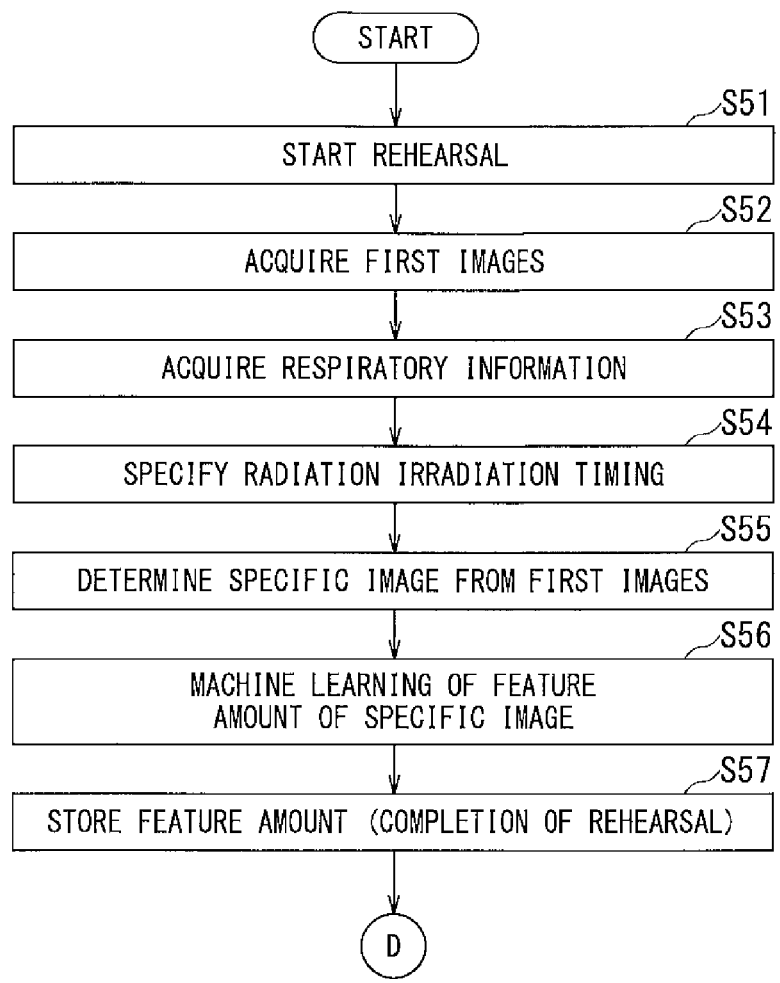
FIG. 14 is a flowchart illustrating the anterior part of the interlock processing to be performed by the moving-object tracking apparatus.
Figure 15:
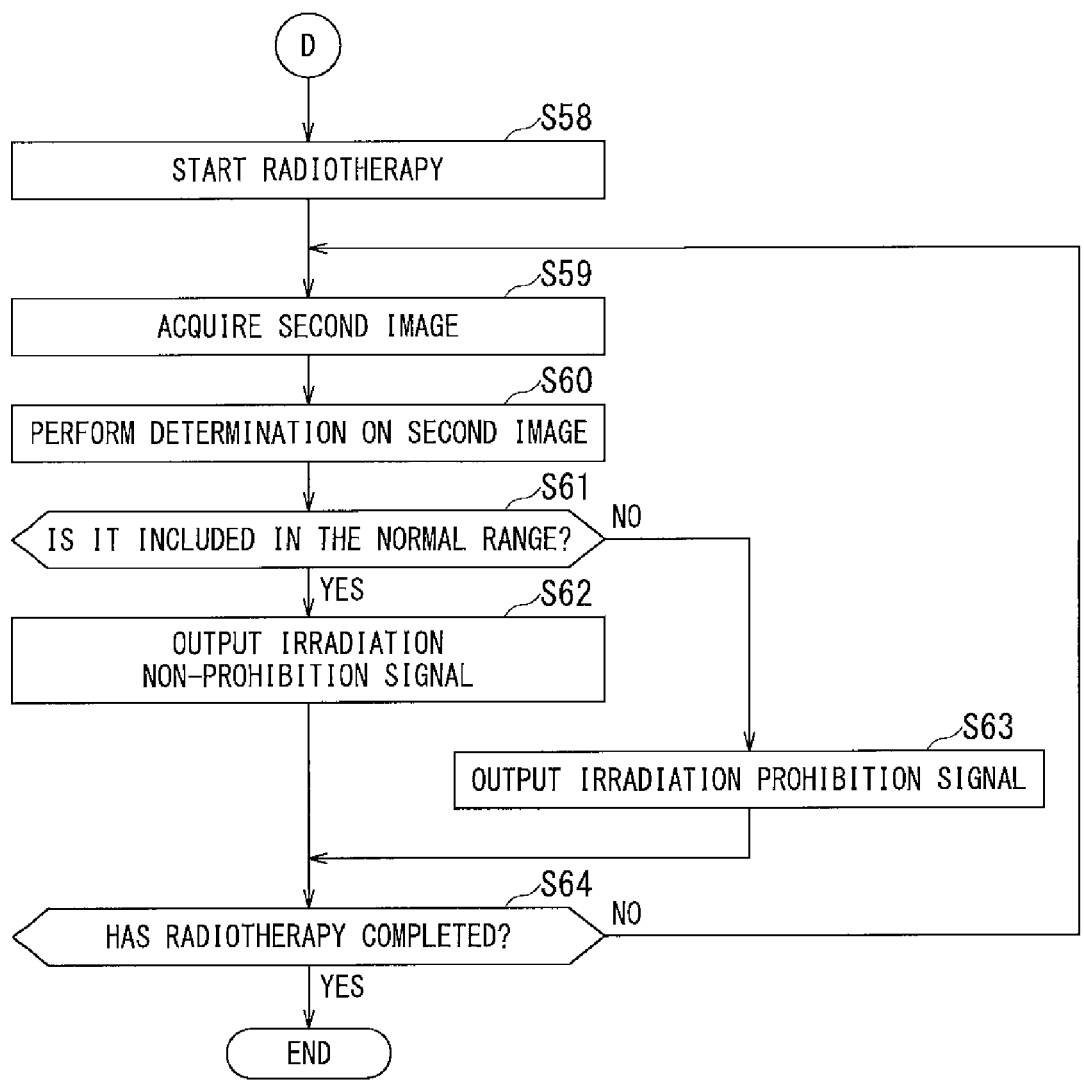
FIG. 15 is a flowchart illustrating the posterior part of the interlock processing to be performed by the moving-object tracking apparatus.

Hereinbelow, a description will be given of the moving-object tracking apparatus (medical image processing apparatus) of the second embodiment by referring to FIG. 13 to FIG. 15. The same reference signs are assigned to the same components as the above-described embodiment in each figure, and duplicate description is omitted. It should be noted that the moving-object tracking apparatus and the medical image processing apparatus are integrally configured in the second embodiment.

Figure 13:
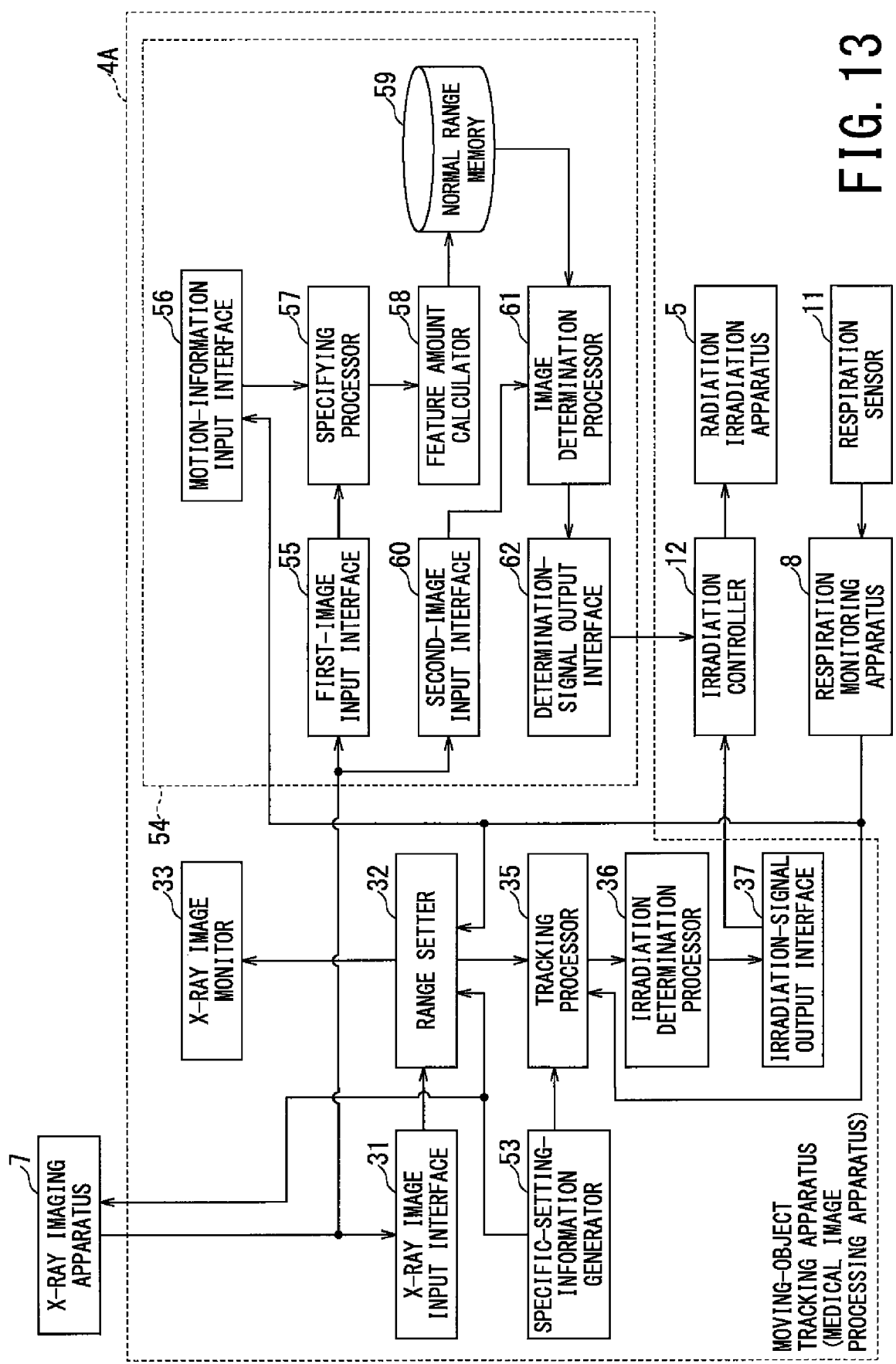
FIG. 13 is a block diagram illustrating the moving-object tracking apparatus of the second embodiment.

As shown in FIG. 13, the moving-object tracking apparatus 4A of the second embodiment includes a specific-setting-information generator 53 configured to generate the specific setting information and an interlock device 54. In the second embodiment, the term "interlock" means to specify a normal state and prohibit radiation irradiation in any other state (i.e., in an abnormal state). In the second embodiment, imaging for generating the X-ray image 40 (FIG. 5) and tracking of the marker M are performed on the basis of the specific setting information which is generated by the specific setting information generator 53. Additionally, the other configuration is almost the same as that of the moving-object tracking apparatus 4 (FIG. 3) of the first embodiment. Although the evaluator 38 and the warning output interface 39 are omitted for illustration in FIG. 13, these components may be provided in the second embodiment. Further, the configuration of the specific-setting-information generator 53 in the second embodiment may have the same configuration as that of the medical image processing apparatus 3 in the first embodiment.

The interlock device 54 of the moving-object tracking apparatus 4A according to the second embodiment is a safety device for preventing the radiation irradiation apparatus 5 from radiating the radioactive rays R when the state is not the normal state.

For instance, the timing suitable for irradiation is assumed to be the timing when the patient P completely exhales (i.e., breathes out). When the state of the patient P is not normal at the timing of breathing out, the patient P is in an abnormal state (e.g., a state that is not normal, such as coughing or sneezing) or it is in an abnormal state in which tracking of the marker M has failed. If radiation irradiation is performed in such an abnormal state, there is a possibility that the radioactive rays R hit a position deviated from the lesion area T.

For this reason, the interlock device 54 determines whether it is in the normal state or not, by using the X-ray images 40. When it is determined to be in the normal state, radiation irradiation is not prohibited. When it is determined to be in an abnormal state (i.e., in any state excluding the normal state), control for prohibiting radiation irradiation is performed. For the determination, the interlock device 54 may use the entirety of at least one X-ray image 40 or other information such as a partial image of the specific position 41 (FIG. 5), a partial image in the vicinity the specific position 41, a partial image in the vicinity of the lesion area T.

The interlock device 54 includes a first-image input interface (i.e., first image acquisition unit) 55, an motion-information input interface (i.e., motion-information acquisition unit) 56, a specifying processor (i.e., specification unit) 57, a feature calculator (i.e., feature acquisition unit) 58, a normal range memory (i.e., normal range storage unit) 59, a second-image input interface (i.e., second image acquisition unit) 60, an image determination processor (i.e., image determination unit) 61, and a determination-signal output interface (i.e., determination-signal output unit) 62.

The first-image input interface 55 acquires first images which are the X-ray images (fluoroscopic images) 40 of the patient (object) P imaged during rehearsal before treatment.

The motion-information input interface 56 acquires the respiratory information (motion information) of the patient P which is acquired by using the respiration monitoring apparatus 8 during rehearsal.

The specifying processor 57 specifies a timing suitable for radiation irradiation on the basis of the respiratory information, and acquires the first image which is generated by imaging the patient P at this specified timing.

The feature calculator 58 acquires feature of the first image acquired by the specifying processor 57, and calculates a normal range which is a range of feature indicative of the normal state.

The normal range memory 59 stores parameters indicative of the calculated normal range.

The second-image input interface 60 acquires second images which are the X-ray images 40 of the patient P imaged at times different from the imaging times of the respective first images (e.g., during radiotherapy).

The image determination processor 61 acquires the feature from the second images, and determines whether the feature is included in the normal range or not, by using the normal range indicated by the parameters being read out from the normal range memory 59.

The determination-signal output interface 62 outputs a determination signal indicating whether it is in the normal state or not, according to the result of the determination.

The parameters representing the normal range are, for instance, parameters of a discriminator. As a discriminator, for instance, a one-class support vector machine, a two-class support vector machine, a neural network, a deep neural network, and decision tree can be used. Another discriminator may be used. The above-described determination is performed by a discriminator. The parameters of the discriminator can be learned by machine learning with the use of the feature indicative of the normal state.

Since plural X-ray images 40 (first images) are generated by time-sequentially and consecutively imaging the patient P during rehearsal, it is possible to generate a moving image by using these plural X-ray images 40. In addition, the respiratory information (motion information) acquired by the motion-information input interface 56 is information correlated with the movement of the lesion area T (i.e., target part of irradiation). Further, the respiratory information is acquired in association with the imaging time of each of the X-ray images 40.

In the present embodiment, the radioactive rays R are radiated when all of the following first to third conditions are satisfied. The first condition is that the respiratory state of the patient P acquired by the respiration monitoring apparatus 8 indicates the timing of breathing out (i.e., completely exhaling). The second condition is that the above-described marker M exists at the specific position 41. The third condition is that the image determination processor 61 of the interlock device 54 determines that the X-ray image 40 is in the normal state.

In addition, the feature calculator 58 of the interlock device 54 acquires the feature of the X-ray images 40 (first images) generated by imaging the patient P during rehearsal before treatment. As the feature, for instance, a vector in which pixel values are arranged is used. The X-ray images 40 used for learning are, e.g., respective images corresponding to several breaths. Since the state in which the patient P is not coughing or sneezing is defined as the normal state, images when the patient P is not coughing or sneezing is selected from these images and used for the learning. An image in the normal state is called a normal image (specific image). Further, the X-ray images 40 may be images generated by imaging the patient P in one direction or plural directions. The feature may be a vector in which the pixel values of the X-ray images 40 (first images) imaged in plural directions are arranged. The selection of images may be performed by a user or may be automatically performed by the interlock device 54 depending on the respiratory information.

In the case of changing the definition of the normal state, the normal image used for learning is also changed. For instance, in the case of defining the state where the marker M appears at the specific position 41 as the normal state, the X-ray images 40 (first images) in this state may be set as normal images to be used for learning. In this definition of the normal state, the motion-information input interface 56 is not required in the interlock device 54. The normal range is, e.g., a hypersphere which encompasses the feature in the normal state in feature space. The larger the size of the hypersphere is, the lower the detection sensitivity of the abnormal state becomes. One-class support vector machine is known as an optimization method for making the radius of the hypersphere as small as possible under the condition that all the vectors which are the feature in the normal state are included. It is possible to automatically set a hypersphere by using this one-class support vector machine. The dimension of the vectors may be compressed by principal component analysis. Among the X-ray images 40 (first images), any image indicating an abnormal state may be set as an abnormal image (i.e., non-specific image), and the discriminator may perform learning under arbitrary supervised learning from the normal images and abnormal images. As the discriminator of supervised learning, for instance, a two-class support vector machine, a neural network, a deep neural network, and a decision tree can be used.

The interlock device 54 determines whether it is in the normal state or not, from the X-ray images 40 (second images) generated by imaging the patient P during radiotherapy. Specifically, the interlock device 54 acquires the feature from the X-ray images 40 (second images), and determines whether the acquired feature is included in the normal range or not, by using the discriminator which is indicated by the parameters being read out from the normal range memory 59.

The moving-object tracking apparatus 4A (interlock device 54) includes artificial intelligence based on machine learning. The normal range may be set as the combined range including both of (a) the normal range being set from only the normal image and (b) the normal range being set from a pair of the normal image and the abnormal image.

Next, a description will be given of the interlock processing (medical image processing method) to be performed by the moving-object tracking apparatus 4A of the second embodiment with reference to FIG. 14 and FIG. 15. This interlocking processing is executed in parallel with the marker tracking processing (FIG. 11 and FIG. 12) of the first embodiment.

First, in the step S51, rehearsal of X-ray imaging of the patient P is started by using the X-ray imaging apparatus 7 of the moving-object tracking apparatus 4A.

In the next step S52 (i.e., first-image acquisition step), the first-image input interface 55 acquires the first images which are the X-ray images 40.

In the next step S53 (i.e., motion-information acquisition step), the motion-information input interface 56 acquires the respiratory information (motion information) of the patient P.

In the next step S54 (i.e., specifying step), on the basis of the respiratory information, the specifying processor 57 specifies the timing which is suitable for radiation irradiation and is the imaging timing (time) of one of the first images.

In the next step S55, the specifying processor 57 determines the normal image (specific image) on the basis of the image of the specific position 41 (FIG. 5) included in the first image imaged at the specified timing.

In the next step S56 (i.e., feature acquisition step), the feature calculator 58 acquires the feature of the normal image and calculates the parameters indicative of the normal range which is the range of the feature indicative of the normal state.

In the next step S57, the normal range memory 59 stores the parameters indicative of the calculated normal range, and thereby the rehearsal is completed.

In the next step S58, radiotherapy using the radiation irradiation apparatus 5 is started.

In the next step S59 (i.e., second-image acquisition step), the second-image input interface 60 acquires the second images which are the X-ray images 40.

In the next step S60, the image determination processor 61 performs determination on the second images on the basis of the normal range which is represented by the parameters stored in the normal range memory 59.

In the next step S61 (i.e., image determination step), as a continuation of this determination, the feature is acquired from the second images and it is determined whether or not the acquired feature is included in the normal range represented by the parameters being read out from the normal range memory 59.

When the feature of the second images is included in the normal range (i.e., when it is determined to be normal in the step S61), the processing proceeds to the step S62 (i.e., signal output step) in which the determination-signal output interface 62 outputs the irradiation non-prohibition signal (i.e., determination signal) to the irradiation controller 12.

Conversely, when the feature of the second images is not included in the normal range (i.e., when it is determined that the feature is not normal in the step S61), the processing proceeds to the step S63 (i.e., signal output step) in which the determination-signal output interface 62 outputs the irradiation prohibition signal (i.e., determination signal) to the irradiation controller 12.

The irradiation controller 12 radiates the radioactive rays R by using the radiation irradiation apparatus 5 on condition that both the irradiation timing signal and the irradiation non-prohibition signal are inputted. Further, even when the irradiation timing signal is inputted, the irradiation controller 12 controls respective components such that irradiation of the radioactive rays R using the radiation irradiation apparatus 5 is not performed in the case of receiving the irradiation prohibition signal.

In the next step S64, the moving-object tracking apparatus 4A determines whether the radiotherapy has completed or not. When the radiotherapy has not been completed, the processing returns to the above-described step S59. On the other hand, when the radiotherapy has been completed, the interlocking processing is terminated.

In the second embodiment, a description has been given of the case where the irradiation prohibition signal and the irradiation non-prohibition signal are outputted to the irradiation controller 12 as one aspect. However, it is not necessary to output the irradiation prohibition signal and the non-irradiation prohibition signal to the outside of the moving-object tracking apparatus 4A. For instance, the irradiation prohibition signal and the irradiation non-prohibition signal may be inputted to the irradiation-signal output interface 37. The irradiation-signal output interface 37 may be configured to output the irradiation timing signal when receiving the irradiation non-prohibition signal (i.e., when there is not input of the irradiation prohibition signal) and to stop output of the irradiation timing signal when receiving the irradiation prohibition signal (i.e., when there is not input of the irradiation non-prohibition signal). When configuration of inputting the irradiation prohibition signal and the irradiation non-prohibition signal to the irradiation-signal output interface 37 is adopted as the moving-object tracking apparatus 4A, the irradiation controller 12 performs irradiation of the radioactive rays R using the radiation irradiation apparatus 5 on condition that the irradiation timing signal is inputted from the irradiation-signal output interface 37.

Although the interlock device 54 is integrally formed with the moving-object tracking apparatus 4A in the second embodiment, the interlock device 54 and the moving-object tracking apparatus 4A may be separately provided.

As described above, the moving-object tracking apparatus (the medical image processing apparatus) of the second embodiment is characterized in including: a first-image input interface configured to acquire a first image which is a fluoroscopic image of a patient imaged by using an imaging apparatus; a motion-information input interface configured to acquire motion information of the patient which is correlated with motion of a target portion of the patient to be subjected to radiation irradiation; a specifying processor configured to specify a timing suitable for the radiation irradiation on the basis of the motion information; a feature calculator configured to acquire feature of the first image generated by imaging the patient at the specified timing and calculate a normal range indicative of a range of feature of a normal state, in which the radiation irradiation is not prohibited, from the feature; a second-image input interface configured to acquire a second image which is a fluoroscopic image of the patient imaged by using the imaging apparatus and is a determination target; an image determination processor configured to perform determination as to whether the feature of the second image is included in the normal range or not; and a determination-signal output interface configured to output a determination signal according to the result of the determination.

The moving-object tracking method (medical image processing method) of the second embodiment is characterized in including: a first image acquisition step of acquiring a first image which is a fluoroscopic image of a patient imaged by using an imaging apparatus; a motion-information acquisition step of acquiring motion information correlated with movement of a target portion of the patient to be subjected to radiation irradiation; a specifying step of specifying a timing suitable for the radiation irradiation on the basis of the motion information; a feature acquisition step of acquiring feature of the first image generated by imaging the patient at the specified timing and calculating a normal range indicative of a range of the feature of a normal state, in which the radiation irradiation is not prohibited, from the feature; a second-image acquisition step of acquiring a second image which is a fluoroscopic image of the patient imaged by using the imaging apparatus and is a determination target; an image determination step of determining whether the feature of the second image is included in the normal range or not; and a signal output step of outputting a determination signal according to a determination result of the image determination step.

In this manner, radiation irradiation in an abnormal state (non-normal state) can be avoided by determining the image of the region corresponding to the specific region included in the second image, which is generated by imaging the patient P using an imaging apparatus during radiotherapy, with the use of the feature. In addition, by making the interlock device 54 perform machine learning of the feature of the first images generated by imaging the patient at the time of treatment planning using the imaging apparatus, labor for setting the normal range at the time of treatment planning can be reduced.

Third Embodiment

Figure 18:
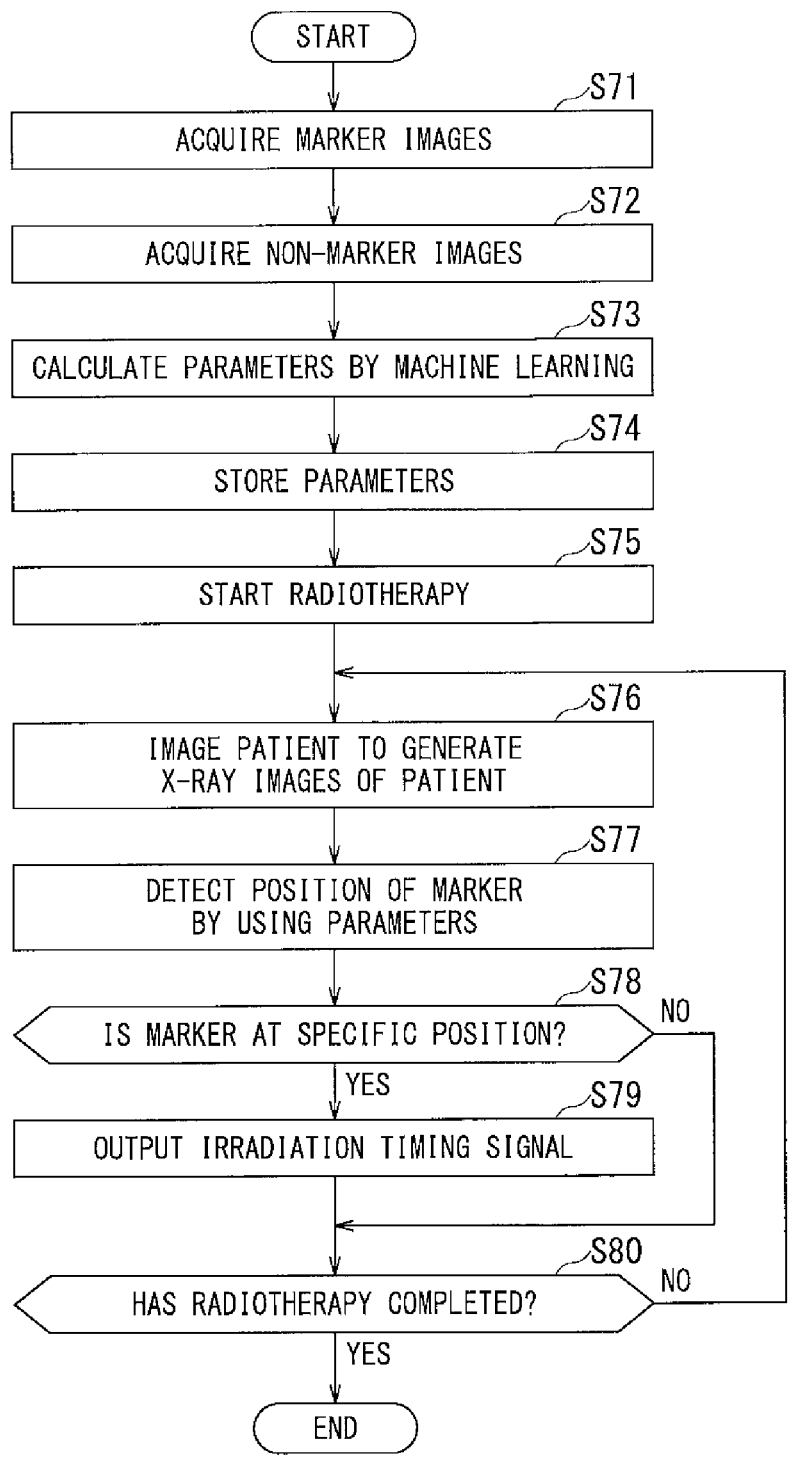
FIG. 18 is a flowchart illustrating the marker tracking processing to be performed by the moving-object tracking apparatus of the third embodiment.

Hereinbelow, a description will be given of the moving-object tracking apparatus (medical image processing apparatus) of the third embodiment by referring to FIG. 16 to FIG. 18. The same reference signs are assigned to the same components as the above-described embodiments in each figure, and duplicate description is omitted. It should be noted that the moving-object tracking apparatus and the medical image processing apparatus are integrally configured in the third embodiment.

Figure 16:
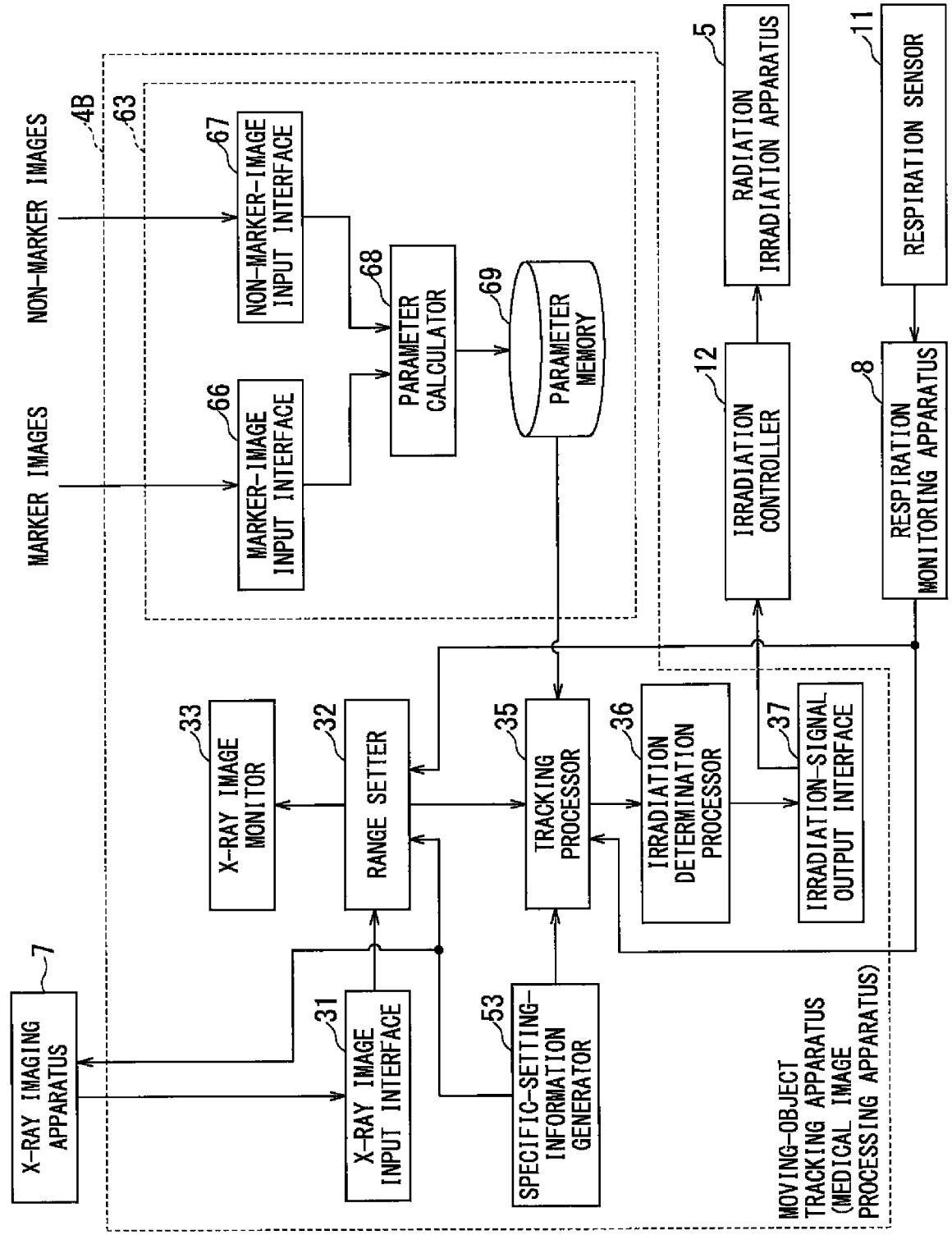
FIG. 16 is a block diagram illustrating the moving-object tracking apparatus of the third embodiment.

As shown in FIG. 16, the moving-object tracking apparatus 4B of the third embodiment includes the specific-setting-information generator 53 configured to generate the specific setting information and a marker learning device 63. In the third embodiment, imaging for generating the X-ray images 40 (FIG. 5) and tracking of the marker M are performed on the basis of the specific setting information generated by the specific-setting-information generator 53. Further, the other configuration of the moving-object tracking apparatus 4B is almost the same as that of the moving-object tracking apparatus 4 (FIG. 3) of the first embodiment.

In the above-described embodiments, the marker M in a spherical shape is exemplified. However, in actual treatment, the marker M having various shapes is used according to the site in the body where the marker M is placed. Additionally, there are various sizes for the marker M. For instance, there are a rod-shaped (coil-shaped) marker M with a diameter of 0.5 mm and a length of 5 mm, a marker M in a clip shape, and a wedge-shaped marker M.

When the respective markers M having these shapes are imaged using X-rays, the images of the respective markers M appearing in the X-ray images 40 differ from each other according to, e.g., orientation of each marker M or the posture of the patient P (FIG. 17). For instance, the rod-shaped marker M is depicted as a circular image when it is placed so as to be parallel to the normal direction with respect to the image surface, and gradually becomes a long bar shape as it is inclined from that position. In this manner, in order to detect the position of the marker M appearing in the X-ray images 40 with the tracking processor 35, it is preferable to cause the marker learning device 63 to learn the images of the respective markers M in advance.

The marker learning device 63 includes: a marker-image input interface (i.e., object-image acquisition unit) 66 configured to acquire a marker image 64 (i.e., object image as shown in FIG. 17A) in which the marker M (learning target) is depicted; a non-marker image input interface (i.e., non-object image acquisition unit) 67 configured to acquire a non-marker image 65 (i.e., non-object image as shown in FIG. 17B) in which the marker M is not depicted; a parameter calculator (i.e., parameter calculation unit) 68 configured to calculate parameters of a discriminator used for identifying the position where the marker M is depicted in an image, on the basis of machine learning; and a parameter memory (i.e., parameter storage unit) 69 configured to store the calculated parameters.

In the moving-object tracking apparatus 4B, the X-ray image input interface (fluoroscopic-image acquisition unit) 31 acquires the X-ray images 40 (fluoroscopic images) of the patient (object)P imaged by using the X-ray imaging apparatus 7 during radiotherapy. Afterward, the tracking processor (position detection unit) 35 detects the position of the marker M appearing in the X-ray images 40 by using the discriminator which is represented by the parameters stored in the parameter memory 69.

As shown in FIG. 17A and FIG. 17B, a large number of marker images 64 and non-marker images 65 are prepared in advance for machine learning. In the respective marker images 64, the markers M in various orientations and the living tissues 70 are depicted. In each of the non-marker images 65, the marker M is not depicted and only the living tissues 70 are depicted. From these marker images 64 and non-marker images 65, the marker learning apparatus 63 generates a discriminator for discriminating between the marker images 64 and the non-marker images 65 by machine learning. The discriminator may be configured to output binary likelihoods (i.e., plausibility) of 0 and 1 indicating whether the marker M is included in the image or not. Additionally or alternatively, the discriminator may be configured to output a likelihood of 0 to 1 indicating the same.

It should be noted that the marker images 64 may be images actually obtained by X-ray imaging of the patient P. In addition, the marker images 64 may be an image generated by CG (Computer Graphics) of a virtual image of the marker M. Further, the marker images 64 may be the DRR images 46 generated on the basis of the geometry information of the X-ray imaging apparatus 7 and the three-dimensional volume image of the patient P in which the marker M is placed. Moreover, the marker images 64 may be the X-ray image s40 of the patient P imaged at the time of rehearsal before treatment or may be the X-ray images 40 of a third person imaged separately from the rehearsal. Furthermore, the marker images 64 may be the DRR images 46 generated from a three-dimensional volume image of a third person.

In addition, the parameter calculator 68 generates a discriminator that discriminates between the marker images 64 and the non-marker images 65 by machine learning. The parameter calculator 68 causes the parameter memory 69 to store a parameter group representing the generated discriminator as parameters for detecting the markers M.

As the discriminator, an arbitrary supervised learning discriminator can be used. For instance, a support vector machine, a neural network, and a decision tree can be used as the discriminator. As the neural network, a deep neural network may be used. As the deep neural network, a convolution neural network may be used. In other words, the moving-object tracking apparatus 4B includes artificial intelligence based on machine learning.

The tracking processor 35 acquires the parameters stored in the parameter memory 69, and acquires the X-ray images 40 from the X-ray image input interface 31. Afterward, the X-ray images 40 are inputted to the discriminator determined by the parameters, and the position of each marker M appearing on each X-ray image 40 is specified on the basis of the likelihood obtained from the discriminator.

Next, a description will be given of the marker tracking processing (medical image processing method) to be performed by the moving-object tracking apparatus 4B of the third embodiment with reference to FIG. 18. Since processing of some steps of the marker tracking processing of the third embodiment is the same as that of the first embodiment, duplicate description is omitted.

First, in the step S71 (i.e., marker image acquisition step), the marker-image input interface 66 acquires the marker images 64 (FIG. 17A), in each of which the marker M is depicted, before start of radiotherapy.

In the next step S72 (i.e., non-marker image acquisition step), the non-marker-image input interface 67 acquires the non-marker images 65 (FIG. 17B), in each of which the marker M is not depicted.

In the next step S73 (i.e., parameter calculation step), the parameter calculator 68 calculates the parameters of the discriminator used for identifying the position of the marker(s) M in the images by machine learning.

In the next step S74, the parameter memory 69 stores the calculated parameters.

In the next step S75, radiotherapy using the radiation irradiation apparatus 5 is started.

In the next step S76 (i.e., fluoroscopic-image acquisition step), the X-ray imaging apparatus 7 images the patient P so as to generate the X-ray images 40 of the patient P and then the X-ray image input interface 31 acquires the X-ray images 40 from the X-ray imaging apparatus 7.

In the next step S77 (i.e., position detection step), the tracking processor 35 detects the position of the marker(s) M appearing in each X-ray image 40 by using the discriminator which is determined from the parameters stored in the parameter memory 69.

In the next step S 78, the tracking processor 35 determines whether the detected marker M is at the specific position 41 (FIG. 5) or not. When the marker M is not located at the specific position 41, the processing proceeds to the step S80 to be described below. Conversely, when the marker M is at the specific position 41, the processing proceeds to the step S79 in which the irradiation-signal output interface 37 outputs the irradiation timing signal to the irradiation controller 12 and then the processing proceeds to the step S80.

In the step S80, the moving-object tracking apparatus 4B determines whether the radiotherapy has completed or not. When the radiotherapy has not been completed, the processing returns to the step S76 as described above. Conversely, when the radiotherapy is completed, the marker tracking process is completed.

Although the marker learning device 63 is integrally formed with the moving-object tracking apparatus 4B in the above-described case, the marker learning device 63 and the moving-object tracking apparatus 4B may be separately provided in the third embodiment. In the third embodiment, a description has been given of the case where the marker images 64 (i.e., images depicting the marker M) and the non-marker images 65 (i.e., images in which the marker M is not depicted) are used as the teacher data at the time of learning for generating a discriminator which outputs a likelihood indicative of whether the marker M is included in the image or not. However, the teacher data may be changed depending on what is to be identified by the discriminator. For instance, in the case of generating a discriminator which outputs the likelihood indicative of whether the marker M is depicted in the vicinity of the center of the image or not, each image in which the marker M appears near the center of the image may be prepared as a marker image 64 while all the other images are prepared as the non-marker images 65. In this case, the non-marker images 65 include images depicting the marker M at the edge of the image and images in which the marker M is not depicted.

Although the marker learning device 63 learns images depicting the marker M in order to track the marker M (learning target) for radiotherapy in the third embodiment, this technique may be applied to other embodiments. For instance, this technique can also be applied to processing of learning images which depict a guidewire, in order to track the guidewire (learning target) in catheter treatment.

A catheter is a medical instrument and is a hollow tube. In catheter treatment, a catheter is inserted into a patient's body (such as inside of a blood vessel and inside of an internal organ), and body fluid is discharged or a stent balloon for vasodilation is sent. In addition, a guidewire is used for operation of the catheter.

For instance, a guidewire is inserted in the body in advance, and a catheter is advanced by this guidewire. Here, time-sequential X-ray images of a patient are generated on a real-time basis and the catheter is advanced while the doctor confirms the position of the guidewire with the real-time X-ray images. Since the guidewire is made of metal, the guidewire appears more clearly than the body tissue in the X-ray images similarly to the marker M of the third embodiment. Since the guidewire is in the shape of a wire, the image of its tip portion is similar to the image of the rod-shape marker M. Thus, it is possible to automatically track the position of the tip of the guidewire in the X-ray images by causing the discriminator to perform machine learning of the image of the guidewire in a manner similar to the third embodiment.

As described above, the moving-object tracking apparatus (medical image processing apparatus) of the third embodiment is characterized in including: an object-image input interface configured to acquire an object image in which a target object or a virtual image of the target object is depicted; a parameter calculator configured to calculate a parameter used for identifying a position where the target object is depicted in an image, on the basis of machine learning by using the object image; a fluoroscopic-image input interface configured to acquire a fluoroscopic image generated by imaging an examinee (e.g., patient) provided with the target object using an imaging apparatus; and a position detector configured to detect a position of the target object depicted in the fluoroscopic image on the basis of the parameter.

The moving-object tracking method (medical image processing method) of the third embodiment is characterized in including: an object-image acquisition step of acquiring an object image in which a target object or a virtual image of the target object is depicted; a parameter calculation step of calculating a parameter used for identifying a position where the target object is depicted in an image, on the basis of machine learning by using the object image; a fluoroscopic-image acquisition step of acquiring a fluoroscopic image generated by imaging an examinee (e.g., patient) provided with the target object using an imaging apparatus; and a position detection step of detecting a position of the target object depicted in the fluoroscopic image on the basis of the parameter.

For instance, in the medical image processing apparatus of conventional technology, it is required to previously register a large number of template images when markers are viewed from various angles and it is also required to compare these template images with fluoroscopic images generated by imaging a patient during radiotherapy. In such conventional technology, there is a problem that load of image processing increases. However, in the third embodiment, such a problem can be solved. In addition, labor for setting various conditions before radiotherapy is saved by using machine learning.

Although the medical image processing apparatuses of embodiments have been described on the basis of the first to third embodiments, the configuration applied in any one of the above-described embodiments may be applied to another embodiment and configurations applied in the respective embodiments may be used in combination. For instance, at least a part of the interlock processing of the second embodiment or the marker tracking process of the third embodiment may be executed in the medical image processing apparatus or the moving-object tracking apparatus of the first embodiment.

The medical image processing apparatus 3 and the moving-object tracking apparatus 4 of the present embodiment includes a storage device such as a ROM (Read Only Memory) and a RAM (Random Access Memory), an external storage device such as a HDD (Hard Disk Drive) and an SSD (Solid State Drive), a display device such as a display, an input device such as a mouse and a keyboard, a communication interface, and a control device which has a highly integrated processor such as a special-purpose chip, an FPGA (Field Programmable Gate Array), a GPU (Graphics Processing Unit), and a CPU (Central Processing Unit). The medical image processing apparatus 3 and the moving-object tracking apparatus 4 can be achieved by hardware configuration with the use of a normal computer.

Note that each program executed in the medical image processing apparatus 3 and the moving-object tracking apparatus 4 of the present embodiment is provided by being incorporated in a memory such as a ROM in advance. Additionally or alternatively, each program may be provided by being stored as a file of installable or executable format in a non-transitory computer-readable storage medium such as a CD-ROM, a CD-R, a memory card, a DVD, and a flexible disk (FD).

In addition, each program executed in the medical image processing apparatus 3 and the moving-object tracking apparatus 4 may be stored on a computer connected to a network such as the Internet and be provided by being downloaded via a network. Further, the medical image processing apparatus 3 and the moving-object tracking apparatus 4 can also be configured by interconnecting and combining separate modules, which independently exhibit respective functions of the components, via a network or a dedicated line.

Although the patient P which is a human being is exemplified as an examination object in the above-described embodiments, the medical image processing apparatus 3 may be used for a case where an animal such as a dog and a cat is the examination object and radiotherapy is performed on the animal.

Although the respiration of the patient P is monitored by using the respiration sensor 11 in the above-described embodiments, the respiration of the patient P may be monitored in another mode. For instance, the respiration of the patient P may be monitored by attaching a reflective marker configured to reflect infrared rays to the body surface of the patient P, irradiating the reflective marker with an infrared laser, and acquiring the reflected wave.

In the above-described embodiments, the medical image processing apparatus 3 displays the X-ray images 40 of the patient P imaged during rehearsal and a user performs selection of the marker M, change of the specific range 45, or change of the specific position 41. However, the moving-object tracking apparatus 4 may be configured such that a user can select the marker M, change the specific range 45, or change the specific position 41 during rehearsal.

Although the plural markers M are placed in the body of the patient P and these markers M are tracked by X-ray imaging in the above-described embodiments, embodiments of the present invention are not limited to such an aspect. For instance, only one marker M may be placed in the body of the patient P and be tracked by X-ray imaging.

Although two pairs of the X-ray irradiators 9 and the X-ray detectors 10 are provided in the above-described embodiments, the marker M may be tracked by using only one pair of the X-ray irradiator 9 and the X-ray detector 10. Further, the marker M may be tracked by using time-sequential X-ray images, each of which is acquired by imaging the patient P from three or more directions with the use of three or more pairs of the X-ray irradiators 9 and the X-ray detectors 10.

Although the specific setting information is generated by generating the DRR images 46 and specifying the position where the marker M appears in the above-described embodiments, the specific setting information may be generated without generating the DRR images 46. Since the information necessary for generating the specific setting information is the position of the marker M, the specific setting information can be generated when the three-dimensional volume image and the geometry information can be acquired.

In the above-described embodiments, a description has been given of the case where the medical image processing apparatus 3 or the moving-object tracking apparatus 4 includes a monitor (i.e., display unit) for displaying images such as the X-ray images 40 and the DRR images 46. However, the medical image processing apparatus of each embodiment may be configured as the medical image processing apparatus 3 which generates and outputs the specific setting information so that the monitor can be omitted.

Although a mode in which each step is executed in series is illustrated in the flowcharts of the present embodiment, the execution order of the respective steps is not necessarily fixed and the execution order of part of the steps may be changed. Additionally, some steps may be executed in parallel with another step.

According to the above-described embodiments, it is possible to save labor of a user related to setting of imaging for generating an image depicting a marker or setting of image processing of this image, by providing a specific-setting-information generator which generates specific setting information used for the setting of imaging for generating the image depicting the marker or the setting of image processing of this image on the basis of three-dimensional volume image and geometry information.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
a discriminator taught by machine learning;
a memory configured to store a parameter of the discriminator by machine learning;
an image input interface configured to acquire a two-dimensional fluoroscopic image of an object subjected to a radiation therapy by irradiating a target portion with radiation;
an image determination processor configured to determine whether a feature of the two-dimensional fluoroscopic image included in a normal range or not, by using the normal range indicated by the discriminator of the parameter; and a determination-signal output interface configured to output a determination signal, the determination signal indicating a result of determination of the image determination processor, wherein at least one first image is used for the machine learning of the discriminator, wherein the at least one first image is either entirety of the two-dimensional fluoroscopic image or part of the two-dimensional fluoroscopic image acquired before starting the radiation therapy and the at least one first image is acquired in a normal state in which the object is breathing out, the image determination processor is configured to determine whether the feature of a second image is included in the normal range or not, by using the noimal range indicated by the discriminator of the parameter read out from the memory, wherein the second image is the two-dimensional fluoroscopic image acquired by the image input interface during the radiation therapy, and the determination-signal output interface is configured to output a determination signal for prohibiting radiation to the target portion when the image determination processor determines that the feature of the second images is not included in the normal range.

2. The medical image processing apparatus according to claim 1, wherein
the discriminator is at least one of: a one-class support vector machine; a two-class support vector machine; a neural network; a deep neural network; a decision tree.

3. The medical image processing apparatus according to claim 1, wherein
the at least one first image includes a plurality of first images that are taken from plural directions during rehearsal of the radiation therapy.

4. The medical image processing apparatus according to claim 1, wherein
the at least first image further includes a first image acquired in an abnormal state in which the object is not breathing out, wherein the first image acquired in the abnormal state is further used for the machine learning of the discriminator.

5. A radiation therapy system comprising:
the medical image processing apparatus according to claim 1;
an imaging apparatus configured to generate a plurality of the two-dimensional fluoroscopic images of the object by serially imaging the object;
a moving-object tracking apparatus including a tracking processor configured to perform image processing of tracking a position of a marker that is depicted in the plurality of the two-dimensional fluoroscopic images of the object generated by the imaging apparatus; and
a radiation apparatus configured to radiate radioactive rays onto a target portion of the radiation in the object when the marker to be tracked by the moving-object tracking apparatus exists at a specific position,
wherein the determination signal outputted from the medical image processing apparatus is used for controlling the radiation apparatus.

6. A medical image processing apparatus comprising:
a discriminator taught by machine learning;
a memory configured to store a parameter of the discriminator;
an image input interface configured to acquire two-dimensional fluoroscopic images of an object subjected to a radiation therapy by irradiating a target portion with radiation; and a position detector configured to detect a position of a marker depicted in the two-dimensional fluoroscopic images on the basis of the discriminator of the parameter, wherein first images, including at least one image in which the marker is depicted and at least one image in which the marker is not depicted, are used for the machine learning of the discriminator, wherein the first images are either entirety of the two-dimensional fluoroscopic images or part of the two-dimensional fluoroscopic images acquired before starting the radiation therapy, the discriminator is configured to output a likelihood indicative of whether the marker is depicted in a second image or not, or the marker is depicted in a vicinity of the center of the second image or not, the second image is a two-dimensional fluoroscopic image acquired by the image input interface during the radiation therapy, and the position detector is configured to detect the position of the marker in the second image based on the likelihood acquire from the discriminator.

7. The medical image processing apparatus according to claim 6, wherein the discriminator is at least one of: a two-class support vector machine; a neural network; a deep neural network; a decision tree.

8. The medical image processing apparatus according to claim 6, wherein the first images are at least one of:
first digital reconstructed images generated based on a three-dimensional volume images generated by imaging the object using a medical examination apparatus and geometry information of an imaging apparatus which is used for imaging the object to generate the two-dimensional fluoroscopic images of the object,
second digital reconstructed images generated based on the three-dimensional volume image of a third person other than the object and the geometry information,
first X-ray images obtained by X-ray imaging of the object,
second X-ray images obtained by X-ray imaging of the third person.

9. The medical image processing apparatus according to claim 6, wherein, in the first images, an image of the marker in included, and the image of the marker is a virtual image of the marker generated by using computer graphics.

10. A radiation therapy system comprising:
the medical image processing apparatus according to claim 6;
an imaging apparatus configured to generate a plurality of the two-dimensional fluoroscopic images of the object by serially imaging the object;
a moving-object tracking apparatus including a tracking processor configured to perform image processing of tracking a position of a marker that is depicted in the plurality of the two-dimensional fluoroscopic images of the object generated by the imaging apparatus; and
a radiation apparatus configured to radiate radioactive rays onto a target portion of the radiation in the object when the marker to be tracked by the moving-object tracking apparatus exists at a specific position,
wherein the tracking processor is configured to detect the position of the marker in the second image based on the likelihood acquire from the discriminator.

* * * * *